United States Patent
Garneau-Tsodikova et al.

(10) Patent No.: US 10,544,112 B2
(45) Date of Patent: Jan. 28, 2020

(54) IDENTIFICATION OF EBSULFUR ANALOGUES WITH BROAD-SPECTRUM ANTIFUNGAL ACTIVITY

(71) Applicant: University of Kentucky Research Foundation, Lexington, KY (US)

(72) Inventors: Sylvie Garneau-Tsodikova, Lexington, KY (US); Huy X. Ngo, Lexington, KY (US); Sanjib K. Shrestha, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/940,544

(22) Filed: Mar. 29, 2018

(65) Prior Publication Data

US 2018/0282291 A1 Oct. 4, 2018

Related U.S. Application Data

(60) Provisional application No. 62/478,403, filed on Mar. 29, 2017.

(51) Int. Cl.
| | | |
|---|---|---|
| *C07D 275/06* | (2006.01) | |
| *A61P 31/10* | (2006.01) | |
| *A01N 43/80* | (2006.01) | |

(52) U.S. Cl.
CPC ........... *C07D 275/06* (2013.01); *A01N 43/80* (2013.01); *A61P 31/10* (2018.01)

(58) Field of Classification Search
CPC ........ A01N 43/80; A61P 31/10; C07D 275/06
See application file for complete search history.

(56) References Cited

FOREIGN PATENT DOCUMENTS

WO    WO 2018/059606    *   4/2018   ............. A01N 43/80

OTHER PUBLICATIONS

Gopinath, P., et al., Broad spectrum anti-infective properties of benzisothiazolones and the parallels in their anti-bacterial and anti-fungal effects, Bioorganic & Medicinal Chemistry Letters, 27(5), 1291-1295 (2017). (Year: 2017).*
Huy X. Ngo, et al., Identification of Ebsulfur Analogues with Broad-Spectrum Antifungal Activity, ChemMedChem 2016, 11, 1507-1516. (Year: 2016).*
United States Environmental Protection Agency (EPA), "Ecological Effects Test Guidelines: OCSPP 850.3020: Honey Bee Acute Contact Toxicity Test," EPA 712-C-019, Jan. 2012 (14 pages).
Lynch et al., "Development of Ebselen, a Glutathione Peroxidase Mimic, for the Prevention and Treatment of Noise-Induced Hearing Loss," Seminars in Hearing, 2009, pp. 47-55, vol. 30, No. 1 (nine (9) pages).
Lin et al., "Aspergillosis Case-Fatality Rate: Systematic Review of the Literature," Clinical Infectious Diseases, Feb. 1, 2001, pp. 358-366, vol. 32, No. 3 (nine (9) pages).
Walsh et al., "Treatment of Aspergillosis: Clinical Practice Guidelines of the Infectious Diseases Society of America," Clinical Infectious Diseases, Feb. 1, 2008, pp. 327-360, vol. 46, No. 3 (34 pages).
Miorelli et al., "Antioxidant and anti-mutagenic effects of ebselen in yeast and in cultured mammalian V79 cells," Mutagenesis, Feb. 10, 2008, pp. 93-99, vol. 23, No. 2 (seven (7) pages).
Bueno et al., "Cytotoxicity and Genotoxicity Evaluation of Organochalcogens in Human Leucocytes: A Comparative Study between Ebselen, Diphenyl Diselenide, and Diphenyl Ditelluride," BioMed Research international, 2013, pp. 1-6, vol. 2013 (seven (7) pages).
Vasan et al., "Inhibitors of the Salicylate Synthase (MbtI) from Mycobacterium tuberculosis Discovered by High-Throughput Screening," ChemMedChem, 2010, pp. 2079-2087, vol. 5, No. 12 (nine (9) pages).
Pappas et al., "Clinical Practice Guideline for the Management of Candidiasis: 2016 Update by the Infectious Diseases Society of America," Clinical Infectious Diseases, Feb. 15, 2016, pp. e1-e50, vol. 62, No. 4 (50 pages).
Cronin et al., "Safety of triazole antifungal drugs in patients with cancer," Journal of Antimicrobial Chemotherapy, 2010, pp. 410-416, vol. 65 (seven (7) pages).
Hughes et al., "Interactions between antifungal and antiretroviral agents," Expert Opin. Drug Saf., 2010, pp. 723-742, vol. 9, No. 5 (20 pages).
Lortholary et al., "Recent Exposure to Caspofungin or Fluconazole Influences the Epidemiology of Candidemia: a Prospective Multicenter Study Involving 2,441 Patients," Antimicrobial Agents and Chemotherapy, Feb. 2011, pp. 532-538, vol. 55, No. 2 (seven (7) pages).
Yamaguchi et al., "Ebselen in Acute Ischemic Stroke: A Placebo-Controlled, Double-blind Clinical Trial," Stroke, 1998, pp. 12-17, vol. 29 (seven (7) pages).
Singh et al., "The resurgence of covalent drugs," Nature Reviews Drug Discovery, Apr. 2011, pp. 307-317, vol. 10.
Azad et al., "Ebselen induces reactive oxygen species (ROS)-mediated cytotoxicity in Saccharomyces cerevisiae with inhibition of glutamate dehydrogenase being a target," FEBS Open Bio, 2014, pp. 77-89, vol. 4 (13 pages).
Rex et al., Reference Method for Broth Dilution Antifungal Susceptibility Testing of Yeasts; Approved Standard—Third Edition, Clinical and Laboratory Standards Institute (CLSI), 2008, M27-A3, vol. 28, No. 14 (seven (7) pages).
Barber, "Methicillin-resistant staphylococci," J. clin. Path., Feb. 21, 1961, pp. 385-393, vol. 14 (nine (9) pages).
Dantes et al., "National Burden of Invasive Methicillin-Resistant Staphylococcus aureus Infections, United States, 2011," JAMA Internal Medicine, Nov. 25, 2013, pp. 1970-1978, vol. 173, No. 21 (nine (9) pages).

(Continued)

*Primary Examiner* — Erich A Leeser
(74) *Attorney, Agent, or Firm* — Crowell & Moring LLP

(57) ABSTRACT

The invention relates to novel ebsulfur analogues and novel pharmaceutical compositions comprising ebsulfur analogues. The invention also relates to novel methods of treating infections caused by fungal species comprising administration of ebselen, ebsulfur, and ebsulfur analogues.

9 Claims, 3 Drawing Sheets

(56) References Cited

OTHER PUBLICATIONS

Harris, "Methicillin-resistant Staphylococcus aureus (MRSA) (Beyond the Basics)", UpToDate, 2016, https://web.archive.org/web/20160318066312/https://www.uptodate.com/contents/methicillin-resistant-staphylococcus-aureus-mrsa-beyond-th-basics, retrieved Aug. 16, 2019 (four (4) pages).
Boucher et al., "Bad Bugs, No Drugs: No Eskape! An Update from the Infectious Diseases Society of America," Clinical Infectious Diseases, Jan. 1, 2009, pp. 1-12, vol. 48 (12 pages).
Lepri et al., "Indole Based Weapons to Fight Antibiotic Resistance: A Structure-Activity Relationship Study," Journal of Medicinal Chemistry, Jan. 12, 2016, pp. 867-891, vol. 59 (25 pages).
Herzog et al., "6-Thioether Tobramycin Analogues: Towards Selective Targeting of Bacterial Membranes," Angew. Chem. Int. Ed., 2012, pp. 5652-5656, vol. 51 (five (5) pages).
Hafkin et al., "Efficacy and Safety of AFN-1252, the First Staphylococcus-Specific Antibacterial Agent, in the Treatment of Acute Bacterial Skin and Skin Structure Infections, Including Those in Patients with Significant Comorbidities," Antimicrobial Agents and Chemotherapy, Mar. 2016, pp. 1695-1701, vol. 60, No. 3 (seven (7) pages).
Singh et al., "A safe lithium mimetic for bipolar disorder," Nature Communications, Jan. 8, 2013, pp. 1-7, vol. 4 (seven (7) pages.
Bhowmick et al., "Highly Efficient Glutathione Peroxidase and Peroxiredoxin Mimetics Protect Mammalian Cells against Oxidative Damage," Angew. Chem. Int. Ed., 2015, pp. 8449-8453, vol. 54 (five (5) pages).
Nozawa et al., "Susceptibility of Methicillin-Resistant Staphylococcus aureus to the Selenium-Containing Compound 2-Phenyl-1,2-Benzoisoselenazol-3(2H)-One (PZ51)," Antimicrobial Agents and Chemotherapy, Aug. 1989, pp. 1388-1390, vol. 33, No. 8 (three (3) pages).
Favrot et al., "Inactivation of the Mycobacterium tuberculosis Antigen 85 Complex by Covalent, Allosteric Inhibitors," The Journal of Biological Chemistry, Sep. 5, 2014, pp. 25031-25040, vol. 289, No. 36 (11 pages).
Bender et al., "A small-molecule antivirulence agent for treating Clostridium difficile infection," Science Translational Medicine, Sep. 23, 2015, pp. 1-11, vol. 7, No. 306 (12 pages).
Gajadeera et al., "Antimycobacterial activity of DNA intercalator inhibitors of Mycobacterium tuberculosis primase DnaG," The Journal of Antibiotics, 2015, pp. 153-157, vol. 68 (five (5) pages).
Schnuch et al., "Patch testing with preservatives, antimicrobials and industrial biocides. Results from a multicenter study," British Journal of Dermatology, 1998, pp. 467-476, vol. 138 (10 pages).
Du et al., "In Vitro Neurotoxicity of Methylisothiazolinone, a Commonly Used Industrial and Household Biocide, Proceeds via a Zinc and Extracellular Signal-Regulated Kinase Mitogen-Activated Protein Kinase-Dependent Pathway," The Journal of Neuroscience, Sep. 1, 2002, pp. 7408-7416, vol. 22, No. 17 (nine (9) pages).
Benhamou et al., "Di-N-Methylation of Anti-Gram-Positive Aminoglycoside-Derived Membrane Disruptors Improves Antimicrobial Potency and Broadens Spectrum to Gram-Negative Bacteria," Angew. Chem. Int. Ed., 2015, pp. 13617-13621, vol. 54 (five (5) pages).
Bera et al., Antibacterial Activities of Aminoglycoside Antibiotics-Derived Cationic Amphiphiles. Polyol-Modified Neomycin B-, Kanamycin A-, Amikacin-, and Neamine-Based Amphiphiles with Potent Broad Spectrum Antibacterial Activity, Journal of Medicinal Chemistry, 2010, pp. 3626-3631, vol. 53 (six (6) pages).
Motyl et al., "Basic Microbiological Techniques Used in Antibacterial Drug Discovery," Current Protocols in Pharmacology, 2005, pp. 13A.3.1-13A.3.22 (22 pages).
Bjarnsholt, "The Role of Bacterial Biofilms in Chronic Infections," APMIS, 2013, pp. 1-58, (58 pages).
Dartois et al., "Systemic Antibacterial Activity of Novel Synthetic Cyclic Peptides," Antimicrobial Agents and Chemotherapy, Aug. 2005, pp. 3302-3310, vol. 49, No. 8 (nine (9) pages).

Uziel et al., "Transcriptional Regulation of the Staphylococcus aureus Thioredoxin and Thioredoxin Reductase Genes in Response to Oxygen and Disulfide Stress," Journal of Bacteriology, Jan. 2004, pp. 326-334, vol. 186, No. 2 (nine (9) pages).
Gustafsson et al., "Bacillus anthracis Thioredoxin Systems, Characterization and Role as Electron Donors for Ribonucleotide Reductase," The Journal of Biological Chemistry, Nov. 16, 2012, pp. 39686-39697, vol. 287, No. 47 (13 pages).
Scharf et al., "Thioredoxin Is an Essential Protein Induced by Multiple Stresses in Bacillus subtilis," Journal of Bacteriology, Apr. 1998, pp. 1869-1877, vol. 180, No. 7 (nine (9) pages).
Li et al., "Diorcinol D Exerts Fungicidal Action against Candida albicans through Cytoplasm Membrane Destruction and ROS Accumulation," PLoS ONE, Jun. 5, 2015, pp. 1-16, vol. 10, No. 6 (16 pages).
Wang et al., "Copper-Catalyzed Intramolecular N-S Bond Formation by Oxidative Dehydrogenative Cyclization," The Journal of Organic Chemistry, 2013, pp. 7337-7342, vol. 78 (six (6) pages).
Brahemi et al., "Exploring the Structural Requirements for Inhibition of the Ubiquitin E3 Ligase Breast Cancer Associated Protein 2 (BCA2) as a Treatment for Breast Cancer," Journal of Medicinal Chemistry, 2010, pp. 2757-2765, vol. 53, No. 7 (nine (9) pages).
Kamigata et al., "Photochemical Ring-expansion Reaction of 1,2-Benzisothiazolinones," Bull. Chem. Soc. Jpn., Nov. 1985, pp. 3131-3136, vol. 58, No. 11 (six (6) pages).
Bhakuni et al., "An efficient copper mediated synthetic methodology for benzo[d]isothiazol-3(2H)-ones and related sulfur-nitrogen heterocycles," Tetrahedron Letters, 2012, pp. 1354-1357, vol. 53 (four (4) pages).
Correa et al., "Novel Alternative for the N-S Bond Formation and Its Application to the Synthesis of Benzisothiazol-3-ones," Organic Letters, 2006, pp. 4811-4813, vol. 8, No. 21 (three (3) pages).
Sarma et al., "Redox Regulation of Protein Tyrosine Phosphatase 1B (PTP1B): A Biomimetic Study on the Unexpected Formation of a Sulfenyl Amide Intermediate," J. Am. Chem. Soc., 2007, pp. 8872-8881, vol. 129, No. 28 (10 pages).
Pietka-Ottlik et al., "Crucial Role of Selenium in the Virucidal Activity of Benzisoselenazol-3(2H)-ones and Related Diselenides," Molecules, 2010, pp. 8214-8228, vol. 15 (15 pages).
Sano et al., "A Practical Synthesis of N-Substituted 1,2-Benzisothiazolin-3-ones from N,N'-Disubstituted 2,2'-Dithiodibenzamides," Synthesis, 2004, pp. 1585-1588, No. 10 (four (4) pages).
Uchida et al., "The Thermal Decomposition of N,O-Diacyl-N-t-butylhydroxylamines. III. Novel Routes to 2-Substituted 1,2-Benzisothiazol-3-(2H)-ones," Bull. Chem. Soc. Jpn., Apr. 1982, pp. 1183-1187, vol. 55, No. 4 (five (5) pages).
Harris, "Methicillin-resistant Staphylococcus aureus (MRSA) (Beyond the Basics)," UpToDate 2019, https:/www.uptodate.com/contents/methicillin-resilstant-staphyococcus-aureus-mrsa-beyond-the-basics/print, retrieved Aug. 15, 2019 (nine (9) pages).
Ngo et al., "A complex game of hide and seek: the search for new antifungals," Med. Chem. Commun. 2016, pp. 1285-1306, vol. 7 (22 pages).
Su et al., "Ebsulfur as a potent scaffold for inhibition and labelling of New Delhi metallo-β-lactamase-1 in vitro and in vivo," Bioorganic Chemistry, 2019, pp. 192-201, vol. 84 (10 pages).
Lu et al., "Ebsulfur Is a Benzisothiazolone Cytocidal Inhibitor Targeting the Trypanothione Reductase of Trypanosoma brucei," The Journal of Biological Chemistry, Sep. 20, 2013, pp. 27456-27468, vol. 288, No. 38 (14 pages).
White et al., "Identification of Small-Molecule Inhibitors of the Ribonuclease H2 Enzyme," Journal of Biomolecular Screening, 2013, pp. 610-620, vol. 18, No. 5 (11 pages).
Abdul-Hay et al., "Selective Targeting of Extracellular Insulin-Degrading Enzyme by Quasi-Irreversible Thiol-Modifying Inhibitors," ACS Chemical Biology, 2015, pp. 2716-2724, vol. 10 (nine (9) pages).
Price et al., "Molecular Mechanism of Action of Antimalarial Benzoisothiazolones: Species-Selective Inhibitors of the Plasmodium spp. MEP Pathway enzyme, IspD," Scientific Reports, Nov. 18, 2016, pp. 1-12, vol. 6, No. 36777 (12 pages).
Li et al., "An efficient approach to construct benzisothiazol-3(2H)-ones via copper-catalyzed consecutive reaction of 2-halobenzamides

(56) References Cited

OTHER PUBLICATIONS and carbon disulfide," Organic & Biomolecular Chemistry, 2016, pp. 6297-6303, vol. 14 (seven (7) pages).
Dahl et al., "Potent, Selective, and Orally Available Benzoisothiazolone Phosphomannose Isomerase Inhibitors as Probes for Congenital Disorder of Glycosylation Ia," Journal of Medicinal Chemistry, May 3, 2011, pp. 3661-3668, vol. 54 (eight (8) pages).
Gopinath et al., "Benzisothiazolones arrest the cell cycle at the $G_2/M$ phase and induce apoptosis in HeLa cells," Med. Chem. Commun., 2013, pp. 749-752, vol. 4 (four (4) pages).
Liu et al., "Design, synthesis and evaluation of 1,2-benzisothiazol-3-one derivatives as potent caspase-3 inhibitors," Bioorganic & Medicinal Chemistry, 2013, pp. 2960-2967, vol. 21 (eight (8) pages).
Sharlow et al., "A Target-Based High Throughput Screen Yields Trypanosoma brucei Hexokinase Small Molecule Inhibitors with Antiparasitic Activity," PLoS Neglected Tropical Diseases, Apr. 2010, pp. 1-8, vol. 4, No. 4 (eight (8) pages).
Zou et al., "Synergistic antibacterial effect of silver and ebselen against multidrug-resistant Gram-negative bacterial infections," EMBO Molecular Medicine, 2017, pp. 1165-1178, vol. 9, No. 8 (14 pages).
Wang et al. "Developing selective histone deacetylases (HDACs) inhibitors through ebselen and analogs," Drug Design, Development and Therapy, 2017, pp. 1369-1382, vol. 11 (14 pages).
Lu et al., "Inhibition of bacterial thioredoxin reductase: an antibiotic mechanism targeting bacteria lacking glutathione," The FASEEB Journal, 2013, pp. 1394-1403, vol. 27 (10 pages).
Capper et al., "The cysteine-reactive small molecule ebselen facilitates effective SOD1 maturation," Nature Communications, 2018, pp. 1-9, vol. 9, No. 1693 (nine (9) pages).
Mukherjee et al., "Ebselen Inhibits Hepatitis C Virus NS3 Helicase Binding to Nucleic Acid and Prevents Viral Replication," ACS Chemical Biology, Aug. 6, 2014, pp. 2393-2403, vol. 9 (11 pages).
Pratta et al., "Effect of ebselen on IL-1-induced alterations in cartilage metabolism," Inflammation Research, 1998, pp. 115-121, vol. 47 (seven (7) pages).
Thangamani et al., "Repurposing ebselen for treatment of multidrug-resistant staphylococcal infections," Scientific Reports, Jun. 26, 2015, pp. 1-13, vol. 5, No. 11596 (13 pages).
De Munnik et al., "Targeting the Mycobacterium tuberculosis transpeptidase $Ldt_{Mt2}$ with cysteine-reactive inhibitors including ebselen," Chem. Commun., 2019, (four (4) pages).
Leroux et al., "Identification of ebselen as a potent inhibitor of insulin degrading enzyme by a drug repurposing screening," European Journal of Medicinal Chemistry, 2019, pp. 557-566, vol. 179 (10 pages).
Marshall et al., "Structure, Mechanism, and Inhibition of Aspergillus fumigatus Thioredoxin Reductase," Antimicrobial Agents and Chemotherapy, Mar. 2019, pp. 1-15, vol. 63, No. 3 (15 pages).
Ruan et al., "Kidney-Type Glutaminase Inhibitor Hexylselen Selectively Kills Cancer Cells via a Three-Pronged Mechanism," ACS Pharmacology & Translational Science, Jan. 11, 2019, pp. 18-30, vol. 2 (13 pages).
Garland et al., "Covalent Modifiers of Botulinum Neurotoxin Counteract Toxin Persistence," ACS Chemical Biology, 2019, pp. 76-87, vol. 14 (12 pages).
Wall et al., "Screening a Repurposing Library for Inhibitors of Multidrug-Resistant Candida auris Identifies Ebselen as a Repositionable Candidate for Antifungal Drug Development," Antimicrobial Agents and Chemotherapy, Oct. 2018, pp. 1-13, vol. 62, No. 10 (13 pages).
Hu et al., "Design, synthesis, and biological evaluation of histone deacetylase inhibitors possessing glutathione peroxidase-like and antioxidant activities against Alzheimer's disease," Bioorganic & Medicinal Chemistry, 2018, pp. 5718-5729, vol. 26 (12 pages).
Abdelkhalek et al., "Repurposing ebselen for decolonization of vancomycin-resistant enterococci (VRE)," PLoS ONE, Jun. 28, 2018, pp. 1-14, vol. 13, No. 6 (14 pages).
Simanjuntak et al., "Ebselen alleviates testicular pathology in mice with Zika virus infection and prevents its sexual transmission," PLoS Pathogens, Feb. 15, 2018, pp. 1-23, vol. 14, No. 2 (23 pages).
Chen et al., "Target discovery of ebselen with a biotinylated probe," Chem. Commun., 2018, pp. 9506-9509, vol. 54 (four (4) pages).
Jin et al., "Investigation of synergistic antimicrobial effects of the drug combinations of meropenem and 1,2-benzisoselenazol-3(2H)-one derivatives on carbapenem-resistant Enterobacteriaceae producing NDM-1," European Journal of Medicinal Chemistry, 2018, pp. 285-302, vol. 155 (18 pages).
Tang et al., "Aglycone Ebselen and β-D-Xyloside Primed Glycosaminoglycans Co-contribute to Ebselen (β-D-Xyloside-Induced Cytotoxicity," Journal of Medicinal Chemistry, 2018, pp. 2937-2948, vol. 61 (12 pages).
Yu et al., "Ebselen: Mechanisms of Glutamate Dehydrogenase and Glutaminase Enzyme Inhibition," ACS Chemical Biology, Oct. 26, 2017, pp. 3003-3011, vol. 12 (nine (9) pages).
Pacula et al., "New Chiral Ebselen Analogues with Antioxidant and Cytotoxic Potential," Molecules, 2017, pp. 1-15, vol. 22 (15 pages).
Goins et al., "Exploring Covalent Allosteric Inhibition of Antigen 85C from Mycobacterium tuberculosis by Ebselen Derivatives," ACS Infectious Diseases, Mar. 13, 2017, pp. 378-387, vol. 3 (10 pages).
Wang et al., "Synthesis and evaluation of 8-hydroxyquinolin derivatives substituted with (benzo[d][1,2]selenazol-3(2H)-one) as effective inhibitor of metal-induced Aβ aggregation and antioxidant," Bioorganic & Medicinal Chemistry, 2016, pp. 4741-4749 vol. 24 (nine (9) pages).
Macegoniuk et al, "1,2-Benzisoselenazol-3(2H)-one Derivatives As a New Class of Bacterial Urease Inhibitors," Journal of Medicinal Chemistry, Aug. 14, 2016, pp. 8125-8133, vol. 59 (nine (9) pages).
Thangamani et al., "Repurposing Clinical Molecule Ebselen to Combat Drug Resistant Pathogens," PLoS ONE, Jul. 29, 2015, pp. 1-16, vol. 10, No. 7 (16 pages).
Stoyanovsky et al., "Design and Synthesis of a Mitochondria-Targeted Mimic of Glutathione Peroxidase, MitoEbselen-2, as a Radiation Mitigator," ACS Medicinal Chemistry Letters, Nov. 18, 2014, pp. 1304-1307, vol. 5 (four (4) pages).
Linsky et al., "Screening for Dimethylarginine Dimethylaminohydrolase Inhibitors Reveals Ebselen as a Bioavailable Inactivator," ACS Medicinal Chemistry Letters, Jun. 8, 2011, pp. 592-596, vol. 2 (five (5) pages).
Terentis et al., "The Selenazal Drug Ebselen Potently Inhibits Indoleamine 2,3-Dioxygenase by Targeting Enzyme Cysteine Residues," Biochemistry, 2010, pp. 591-600, vol. 49, No. 3 (10 pages).
Zou et al., "Synergistic antibacterial activity of silver with antibiotics correlating with the upregulation of the ROS production," Scientific Reports, Jul. 24, 2018, pp. 1-11, vol. 8, No. 11131 (11 pages).
Arendrup, "Epidemiology of invasive candidiasis," Current Opinion in Critical Care, 2010, pp. 445-452, vol. 16 (eight (8) pages).
Kett et al., "Candida bloodstream infections in intensive care units: Analysis of the extended prevalence of infection in intensive care unit study," Crit Care Med, 2011, pp. 665-670, vol. 39, No. 4 (six (6) pages).
Wisplinghoff et al., "Nosocomial Bloodstream Infections in US Hospitals: Analysis of 24,179 Cases from a Prospective Nationwide Surveillance Study," Clinical Infectious Diseases, Aug. 1, 2004, pp. 309-317, vol. 39 (nine (9) pages).
Kullberg et al., "Invasive Candidiasis," The New England Journal of Medicine, Oct. 8, 2015, pp. 1445-1456, vol. 373, No. 15 (12 pages).
Mayr et al., "Epidemiology and Antifungal Resistance in Invasive Aspergillosis According to Primary Disease—Review of the Literature," European Journal of Medical Research, Apr. 28, 2011, pp. 153-157, vol. 16 (five (5) pages).
Van Der Linden et al., "Prospective Multicenter International Surveillance of Azole Resistance in Aspergillus fumigatus," Emerging Infectious Diseases, Jun. 2015, pp. 1041-1044, vol. 21, No. 6 (four (4) pages).
Sloan et al., "Cryptococcal meningitis: epidemiology and therapeutic options," Clinical Epidemiology, 2014, pp. 169-182, vol. 6 (14 pages).

(56) References Cited

OTHER PUBLICATIONS

Pasko et al., "Fluconazole: A New Triazole Antifungal Agent," DICP, The Annals of Pharmacotherapy, Sep. 1990, pp. 860-867, vol. 24 (eight (8) pages).
Zumbuehl et al., "An Amphotericin B-Fluorescein Conjugate as a Powerful Probe for Biochemical Studies of the Membrane," Angew. Chem. Int. Ed., 2004, pp. 5181-5185, vol. 43 (five (5) pages).
Baginski et al., "Amphotericin B and Its New Derivatives—Mode of Action," Current Drug Metabolism, 2009, pp. 459-469, vol. 10, No. 5 (11 pages).
Morris et al., "Echinocandins in the management of invasive fungal infections, part 1," Am J Health-Syst Pharm, Sep. 15, 2006, pp. 1693-1703, vol. 63 (11 pages).
Sanguinetti et al., "Antifungal drug resistance among Candida species: mechanisms and clinical impact," Mycoses, 2015, pp. 2-13, vol. 58, Suppl. 2 (12 pages).
Kanafani et al., "Resistance to Antifungal Agents: Mechanisms and Clinical Impact," Clinical Infectious Diseases, Jan. 1, 2008, pp. 120-128, vol. 46 (nine (9) pages).
Shah et al., "Impact of Prior Inappropriate Fluconazole Dosing on Isolation of Fluconazole-Nonsusceptible Candida Species in Hospitalized Patients with Candidemia," Antimicrobial Agents and Chemotherapy, Jun. 2012, pp. 3239-3243, vol. 56, No. 6 (five (5) pages).
Ben-Ami et al., "Antibiotic Exposure as a Risk Factor for Fluconazole-Resistant Candida Bloodstream Infection," Antimicrobial Agents and Chemotherapy, May 2012, pp. 2518-2523, vol. 56, No. 5 (six (6) pages).
Hata et al., "Efficacy of Oral E1210, a New Broad-Spectrum Antifungal with a Novel Mechanism of Action, in Murine Models of Candidiasis Aspergillosis, and Fusariosis," Antimicrobial Agents and Chemotherapy, Oct. 2011, pp. 4543-4551, vol. 55, No. 10 (nine (9) pages).
Kontoyiannis et al., "Toward more effective antifungal therapy: the prospects of combination therapy," British Journal of Haematology, 2004, pp. 165-175, vol. 126 (11 pages).
Day et al., "Combination Antifungal Therapy for Cryptococcal Meningitis," The New England Journal of Medicine, Apr. 4, 2013, pp. 1291-1302, vol. 368, No. 14 (12 pages).
Perfect et al., "Clinical Practice Guidelines for the Management of Cryptococcal Disease: 2010 Update by the Infectious Diseases Society of America," Clinical Infectious Diseases, Feb. 1, 2010, pp. 291-322, vol. 50 (32 pages).
Shrestha et al., "A combination approach to treating fungal infections," Scientific Reports, Nov. 23, 2015, pp. 1-11, vol. 5, No. 17070 (11 pages).
Fosso et al., "Synthesis and Bioactivities of Kanamycin B-Derived Cationic Amphiphiles," Journal of Medicinal Chemistry, Nov. 22, 2015, pp. 9124-9132, vol. 58 (nine (9) pages).
Kim et al., "Repurposing FDA approved drugs against the human fungal pathogen, Candida albicans," Annals of Clinical Microbiology and Antimicrobials, 2015, pp. 1-11, vol. 14, No. 32 (11 pages).
Azad et al., "Ebselen, a promising antioxidant drug: mechanisms of action and targets of biological pathways," Mol Biol Rep, 2014, pp. 4865-4879, vol. 41 (15 pages).
Parnham et al., "The early research and development of ebselen," Biochemical Pharmacology, 2013, pp. 1248-1253, vol. 86 (six (6) pages).
Finnin et al., "Transdermal Penetration Enhancers: Applications, Limitations, and Potential," Journal of Pharmaceutical Sciences, Oct. 1999, pp. 955-958, vol. 88, No. 10 (four (4) pages).
Shrestha et al., "Amphiphilic Tobramycin Analogues as Antibacterial and Antifungal Agents," Antimicrobial Agents and Chemotherapy, Aug. 2015, pp. 4861-4869, vol. 59, No. 8 (nine (9) pages).
Deray, "Amphotericin B nephrotoxicity," Journal of Antimicrobial Chemotherapy, 2002, pp. 37-41, vol. 49, Suppl. S1 (five (5) pages).
Moen et al., "Liposomal Amphotericin B: A Review of its Use as Empirical Therapy in Febrile Neutropenia and in the Treatment of Invasive Fungal Infections," Drugs, 2009, pp. 361-392, vol. 69, No. 3 (32 pages).
Dvorak, "Drug-drug interactions by azole antifungals: Beyond a dogma of CYP3A4 enzyme activity inhibition," Toxicology Letters, 2011, pp. 129-132, vol. 202 (four (4) pages).
Wang et al., "Systematic Review and Meta-Analysis of the Tolerability and Hepatotoxicity of Antifungals in Empirical and Definitive Therapy for Invasive Fungal Infection," Antimicrobial Agents and Chemotherapy, Jun. 2010, pp. 2409-2419, vol. 54, No. 6 (11 pages).
Chang et al., "Antifungal amphiphilic aminoglycosides," Med. Chem. Commun., 2014, pp. 1048-1057, vol. 5 (10 pages).
Fosso et al., "Structure-Activity Relationships for Antibacterial to Antifungal Conversion of Kanamycin to Amphiphilic Analogues," The Journal of Organic Chemistry, Mar. 31, 2015, pp. 4398-4411, vol. 80 (14 pages).
Fosso et al., "New trends in the use of aminoglycosides," Med. Chem. Commun., 2014, pp. 1075-1091, vol. 5 (17 pages).
Seyedmousavi et al., "Antifungal Susceptibility Patterns of Opportunistic Fungi in the Genera Verruconis and Ochroconis," Antimicrobial Agents and Chemotherapy, Jun. 2014, pp. 3285-3292, vol. 58, No. 6 (eight (8) pages).
Bugbee et al., "Yield Comparisons and Unique Characteristics of the Dwarf Wheat Cultivar 'USU-Apogee,'" Dwarf Crops, 1999, Paper 10 (five (5) pages).
Chang et al., "Antibacterial to antifungal conversion of neamine aminoglycosides through alkyl modification. Strategy for reviving old drugs into agrofungicides," The Journal of Antibiotics, 2010, pp. 667-672, vol. 63 (six (6) pages).
Ozyigit et al., "Different dose-dependent effects of ebselen in sciatic nerve ischemia-reperfusion injury in rats," Bosnian Journal of Basic Medical Sciences, 2015, pp. 36-43, vol. 15, No. 4 (eight (8) pages).
Ngo et al., "Development ebsulfur analogues as potent antibacterials against methicillin-resistant *Staphylococcus aureus*," Bioorganic & Medicinal Chemistry, 2016, pp. 6298-6306, vol. 24, with Supporting Information (62 pages).
ClinicalTrials.gov, "SPI-1005 for Prevention and Treatment of Chemotherapy Induced Hearing Loss," https://clinicaltrials.gov/ct2/show/NCT01451863?term=ebselen&cond=chemotherapy-induced+hearing+loss&rank=1, retrieved Aug. 16, 2019 (five (5) pages).
ClinicalTrials.gov, "SPI-1005 for the Treatment of Patients With Meniere's Disease," https://clinicaltrials.gov/ct2/show/NCT03325790?term=ebselen&cond=Meniere+Disease&rank=2, retrieved Aug. 16, 2019 (six (6) pages).
ClinicalTrials.gov, "Study to Evaluate SPI-1005 in Adults With Meniere's Disease," htts://clinicatrials.gov/ct2/show/NCT02603081?term.ebselen&cond=Meniere+Disease&rank=1, retrieved Aug. 16, 2019 (five (5) pages).
Ngo et al. "Identification of Ebsulfur Analogues with Broad-Spectrum Antifungal Activity," ChemMedChem 2016, 11, pp. 1507-1516, vol. 11, with Supporting Information (17 pages).
Bugbee et al., "Registration of 'USU-Apogee' Wheat," Crop Science, 1997, pp. 626, vol. 37 (three (3) pages).
Seyedmousavi et al., "Intrapulmonary Posaconazole Penetration at the Infection Site in an Immunosuppressed Murine Model of Invasive Pulmonary Aspergillosis Receiving Oral Prophylactic Regimens," Antimicrobial Agents and Chemotherapy, May 2014, pp. 2964-2967, vol. 58, No. 5 (four (4) pages).
United States Environmental Protection Agency (EPA), "Ecological Effects Test Guidelines: OPPTS 850.3020: Honey Bee Acute Contact Toxicity", "Public Draft" EPA 712-C-96-147, Apr. 1996 (eight (8) pages).

* cited by examiner

IDENTIFICATION OF EBSULFUR ANALOGUES WITH BROAD-SPECTRUM ANTIFUNGAL ACTIVITY

FIELD OF THE INVENTION

The invention relates to small molecule compounds and pharmaceutically acceptable salts thereof that are useful, among other functions, as anti-fungal agents. The invention also relates to the use of these compounds and pharmaceutical compositions in the treatment of patients or crops with fungal infections.

BACKGROUND OF THE INVENTION

Fungal infections have become an emerging public health threat, heightened due to the increasing size of an immunocompromised patient population (Arendrup, M. C. (2010) Epidemiology of invasive candidiasis. *Curr. Opin. Crit. Care* 16, 445-452). This population includes patients with AIDS, primary immune deficiency, and those who are immunocompromised due to chemotherapy or organ and bone marrow transplantation.

Globally, *Candida* species are the predominant cause of invasive systemic fungal infections, with a reported prevalence at 6.9 cases per 1000 patients (Kett, D. H. et al. (2011) Extended prevalence of infection in ICU study (EPIC II) group of investigators *Candida* bloodstream infections in intensive care units: analysis of the extended prevalence of infection in intensive care unit study. *Crit. Care Med.* 39, 665-670). In the United States, *Candida* infections rank fourth among all hospital-acquired systemic infections in intensive care units (Wisplinghoff, H. et al. (2004) Nosocomial bloodstream infections in US hospitals: analysis of 24,179 cases from a prospective nationwide surveillance study. *Clin. Infect. Dis.* 39, 309-317). In most population-based studies, Candida infections represent the seventh to tenth most common bloodstream infections (Kullberg, B. J. and Arendrup, M. C. (2015) Invasive candidiasis. *N. Engl. J. Med.* 373, 1445-1456). Additionally, many patients are now infected with other fungal species, including Aspergillus fumigatus, *Aspergillus nidulans,* and *Cryptococcus neoformans* (Mayr, A. and Lass-Florl, C. (2011) Epidemiology and antifungal resistance in invasive aspergillosis according to primary disease: review of the literature. *Eur. J. Med. Res.* 16, 153-157; van der Linden, J. W. et al., (2015) Prospective multicenter international surveillance of azole resistance in *Aspergillus fumigatus. Emerg. Infect. Dis.* 21, 1041-1044; Sloan, D. J. and Parris, V. (2014) *Cryptococcal meningitis:* epidemiology and therapeutic options. *Clin. Epidemiol.* 6, 169-182).

Common therapeutic agents used to treat fungal infections include azoles (e.g., fluconazole (FLC), itraconazole (ITC), posaconazole (POS), and voriconazole (VOR)), polyenes (e.g., amphotericin B (AmB), nystatin (NYS), and candicidin (CAN)), allylamines (e.g., butenafine, naftifine, and terbinafine), and echinocandins (e.g., micafungin, caspofungin, and anidulafungin). These drugs function by different mechanisms of action: (i) inhibition of the cytochrome P450 enzyme 14α-demethylase (azoles); (ii) introduction of transmembrane channel leading to monovalent ion leakage (polyenes); (iii) inhibition of squalene epoxidase (allylamines); and (iv) inhibition of synthesis of glucan in the fungal cell wall via the enzyme 1,3-β-glucan synthase (echinocandins) (Pasko, M. T. et al. (1990) Fluconazole: a new triazole antifungal agent. *DICP* 1990, 24, 860-867; Zumbuehl, A.et al. (2004) An amphotericin B-fluorescein conjugate as a powerful probe for biochemical studies of the membrane. *Angew. Chem.* 43, 5181-5185; Baginski, M. and Czub, J. (2009) Amphotericin B and its new derivatives-mode of action. *Curr. Drug Metab.* 10,459-469; Morris, M. I. and Villmann, M. (2006) Echinocandins in the management of invasive fungal infections, part 1. *Am. J. Health Syst. Pharm.* 63, 1693-1703).

Due to improper usage of these antifungal agents, such as insufficient dosages and durations of treatment, more drug-resistant fungal strains have evolved (Sanguinetti, M. et al. (2015) Antifungal drug resistance among *Candida* species: mechanisms and clinical impact. *Mycoses* 58 Suppl 2, 2-13.; Kanafani, Z. A. and Perfect, J. R. (2008) Antimicrobial resistance: resistance to antifungal agents: mechanisms and clinical impact. *Clin. Infect. Dis.* 46, 120-128; Shah, D. N. et al. (2012) Impact of prior inappropriate fluconazole dosing isolation of fluconazole-nonsusceptible *Candida* species in hospitalized patients with candidemia. *Antimicrob. Agents Chemother.* 56, 3239-3243). Additionally, new evidence suggests that antibacterials also contribute to the development of fungal resistance. (Ben-Ami, R.et al. (2012) Antibiotic exposure as a risk factor for fluconazole-resistant *Candida* bloodstream infection. *Antimicrob. Agents Chemother.* 56, 2518-2523).

Currently, three strategies have been employed to overcome antifungal drug resistance. The first strategy is the development of compounds with novel mechanisms of action distinct from previous antifungal agents. For instance, compound E1210 was discovered as a novel first-in-class antifungal compound by the Tsukuba Research Laboratories of Eisai Co., Ltd. This compound was discovered to inhibit fungal glycosylphosphatidylinositol (GPI) biosynthesis and validated in murine models of candidiasis, aspergillosis, and fusariosis (Hata, K. et al. (2011) Efficacy of oral E1210, a new broad-spectrum antifungal with a novel mechanism of action, in murine models of candidiasis, aspergillosis, and fusariosis. *Antimicrob. Agents Chemother.* 55, 4543-4551).

The second strategy is the combination of two antifungal agents. In the literature, there are many examples using two compounds in conjunction to produce synergistic antifungal activity and reduce resistance as well as toxicity (Kontoyiannis, D. P. and Lewis, R. E. (2004) Toward more effective antifungal therapy: the prospects of combination therapy. *Br. J. Haematol.* 126, 165-175; Day, J. N. et al. (2013) Combination antifungal therapy for cryptococcal meningitis. *N. Engl. J. Med.* 368, 1291-1302). Specifically, in patients diagnosed with cryptococcal meningitis, the combination therapy of flucytosine and AmB was shown to be essential for successful clinical outcomes (Perfect, J. R. et al. (2010) Clinical practice guidelines for the management of cryptococcal disease: 2010 update by the Infectious Diseases Society of America. *Clin. Infect. Dis.* 50, 291-322). Recently, it was also found that a combination of azoles and analogues of the aminoglycoside antibiotics tobramycin and kanamycin B resulted in favorable synergistic effects against drug-resistant *Candida albicans* strains (Shrestha, S. K., et al. (2015) A combination approach to treating fungal infections. *Sci. Rep.* 5, 17070; Fosso, M. Y. et al. (2015) Synthesis and bioactivities of kanamycin B-derived cationic amphiphiles. *J. Med. Chem.* 58, 9124- 9132).

The third strategy is the use of known compounds for new applications. For example, the decongestant drug octodrine was identified as a broad-spectrum antifungal compound. Kim, K. et al. (2015) Repurposing FDA approved drugs against the human fungal pathogen, *Candida albicans*. *Ann. Clin. Microbiol. Antimicrob.* 14, 32.

BRIEF SUMMARY OF THE INVENTION

The invention is directed to novel ebselen and ebsulfur analogues and novel pharmaceutical compositions comprising ebselen and ebsulfur analogues of formula (I). The invention is also directed to novel methods of treating infections caused by fungal species comprising administration of ebselen, ebsulfur, ebselen analogues, and ebsulfur analogues of formula (I).

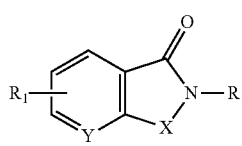

(I)

DETAILED DESCRIPTION OF THE INVENTION

Figure 1A:
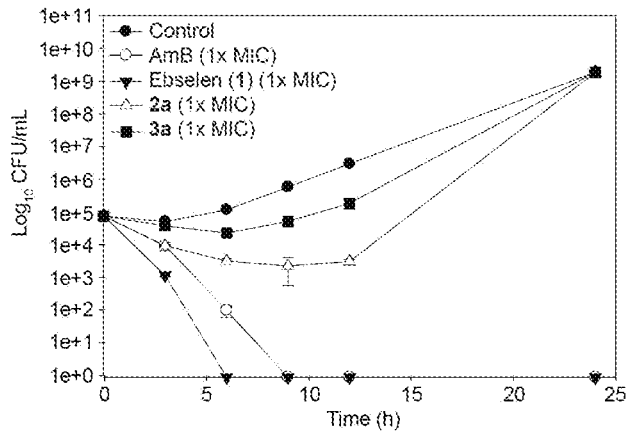
FIG. 1A. Time-kill analysis of ebselen (1) (black inverted triangles), ebsulfur (2a) (white triangles), compound 3a (black squares) was performed at 0, 3, 6, 9, 12, and 24 h. Cultures were exposed to compounds at 1×their respective MIC values. Untreated culture (black circles) was used as the negative control and AmB (white circles) was used the positive control.
Figure 1B:
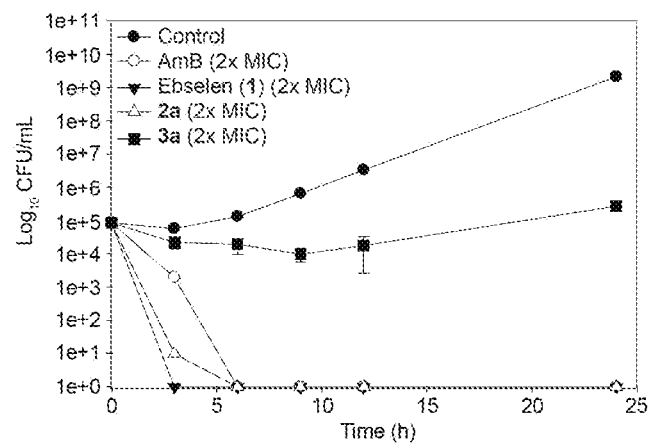
FIG. 1B. Time-kill analysis of ebselen (1) (black inverted triangles), ebsulfur (2a) (white triangles), compound 3a (black squares) was performed at 0, 3, 6, 9, 12, and 24 h. Cultures were exposed to compounds at 2× their respective MIC values. Untreated culture (black circles) was used as the negative control and AmB (white circles) was used the positive control.
Figure 1C:
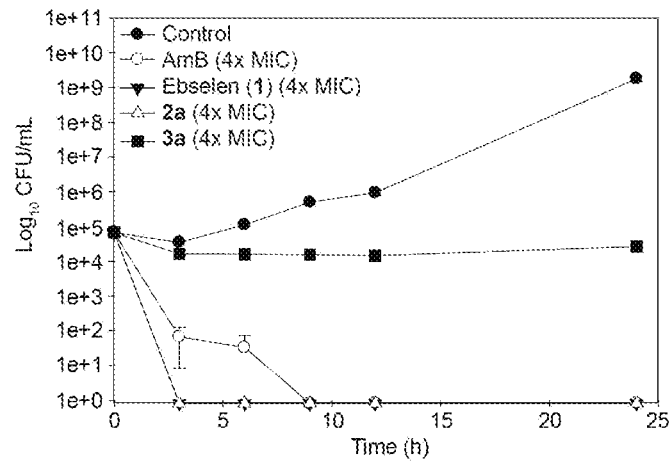
FIG. 1C. Time-kill analysis of ebselen (1) (black inverted triangles), ebsulfur (2a) (white triangles), compound 3a (black squares) was performed at 0, 3, 6, 9, 12, and 24 h. Cultures were exposed to compounds at 4× their respective MIC values. Untreated culture (black circles) was used as the negative control and AmB (white circles) was used the positive control.

Overall, fungal resistance is still relatively uncommon, but this problem is on the rise and expected to become a major healthcare problem. Thus, there is a critical need for the development of novel antifungal compounds.

The invention employs two strategies to overcome antifungal drug resistance: (1) the use of known compounds previously unknown to have anti-fungal activity; and (2) the development of new anti-fungal compounds.

Ebselen is an organoseleno compound, which has completed phase I clinical trial for general safety in human use. Ebselen has diverse therapeutic applications and has been studied in several clinical trials. (Azad, G. K. and Tomar, R. S. (2014) Ebselen, a promising antioxidant drug: mechanisms of action and targets of biological pathways. *Mol. Biol. Rep.* 41, 4865-4879). Ebselen is currently in phase 2 clinical trials for the treatment of chemotherapy-induced hearing loss and Meniere's disease (http://clinicaltrials.gov). Furthermore, ebselen completed a 300-patient phase 3 clinical trial for cerebral ischemia in Japan (Parnham, M. J. and Sies, H. (2013) The early research and development of ebselen. *Biochem. Pharmacol.* 86, 1248-1253). It has been surprisingly discovered that ebselen also exhibits anti-fungal activity.

In addition, the ebsulfur, or 1,2-benzisothiazol-3(2H)-one, scaffold has been shown to exhibit a narrow spectrum of antibacterial activity, i.e., it exhibits activity only against methicillin-resistant *Staphylococcus aureus* (MRSA) (Ngo, H. X. et al. (2016) Development of ebsulfur analogues as potent antibacterials against methicillin-resistant *Staphylococcus aureus*. *Bioorg. Med. Chem.* doi: 10.1016/j.bmc.2016.03.060). It has also been surprisingly discovered that the ebsulfur scaffold also exhibits anti-fungal activity.

Further, due to the structural similarities between ebsulfur and ebselen, it was hypothesized that ebsulfur and its analogues would have a safety profile comparable to that of ebselen. Accordingly, new ebsulfur analogues were prepared for the treatment of fungal infections.

The invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

As used herein, the term "aryl" refers to aromatic groups having 6 to 24 carbon atoms, and "substituted aryl" refers to aryl groups further bearing one or more substituents.

The term "heteroaryl" refers to aromatic groups having 4 to 23 carbon atoms and at least one or more element selected from the group consisting of nitrogen, oxygen, and sulfur; "substituted heteroaryl" refers to heteroaryl groups further bearing one or more substituents.

The term "alkyl" refers to straight or branched chain alkyl radicals having 1 to 20 carbon atoms, and "substituted alkyl" refers to alkyl radicals further bearing one or more substituents.

The term "lower alkyl" refers to straight or branched chain alkyl radicals having in the range of 1 to 4 carbon atoms.

The term "cycloalkyl" refers to cyclic ring-containing moieties containing 3 to 20 carbon atoms, and "substituted cycloalkyl" refers to cycloalkyl moieties further bearing one or more substituents.

The term "pharmaceutically acceptable" refers to a nontoxic material that does not interfere with the effectiveness of the active ingredient(s).

The term "therapeutically effective amount" means an amount of a compound of the invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

Substituted aryl groups, substituted heteroaryl groups, substituted alkyl groups, and substituted cycloalkyl groups are substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —$CO(NR_fR_g)$; wherein each of $R_a$, $R_b$, $R_c$, $R_d$, $R_e$, $R_f$, and $R_g$ are independently selected from H or $C_1$-$C_6$ alkyl.

Salts are acid addition salts, including $Cl^-$, $Br^-$, $I^-$, $NO_2^-$, $HSO_4^-$, $SO_4^-$, $HPO_4^-$, $PO_4^{2-}$, ethanesulfonate, trifluromethane sulfate, p-toluenesulfonate, benzenesulfonate, salicylate, propionate, ascorbate, aspartate, fumarate, galactarate, maleate, citrate, glutamate, glycolate, lactate, malate, maleate, tartrate, oxalate, succinate, and the like.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

As used herein, the term "Formula (I)" may be hereinafter referred to as a "compound(s) of the invention," "the invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The invention provides compounds of formula (I):

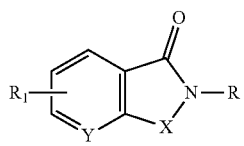

(I)

wherein
X may be Se, S, or S=O;
Y may be C, N, or O;
R may be substituted or unsubstituted aryl, substituted or unsubstituted heteroaryl, substituted or unsubstituted alkyl, substituted or unsubstituted cycloalkyl, or $OR_a$;

$R_1$ may be —H, —OH, —$NH_2$, $OR_b$, $CF_3$, $NO_2$, or CN;
$R_a$ may be linear or branched $C_{1-16}$ alkyl groups or linear pegylated $C_{4-16}$ alkyl groups; and
$R_b$ may be linear or branched $C_{1-16}$ alkyl groups;
or a salt thereof.

A further embodiment of the invention is a compound of formula (I), wherein: X is Se; Y is C; $R_1$ is —H, and R is substituted or unsubstituted aryl, substituted or unsubstituted heteroaryl, substituted or unsubstituted alkyl, or substituted or unsubstituted cycloalkyl; or a salt thereof.

A further embodiment of the invention is a compound of formula (I), wherein: X is Se; Y is C; $R_1$ is —H, and R is substituted or unsubstituted aryl or substituted or unsubstituted heteroaryl; or a salt thereof.

A further embodiment of the invention is a compound of formula (I), wherein: X is Se; Y is C; $R_1$ is —H, and R is substituted or unsubstituted aryl; or a salt thereof.

A further embodiment of the invention is a compound of formula (I), wherein: X is Se; Y is C; $R_1$ is —H, and R is a substituted or unsubstituted aryl selected from the group consisting of substituted or unsubstituted phenyl, substituted or unsubstituted naphthalene, substituted or unsubstituted anthracene, substituted or unsubstituted phenanthrene, and substituted or unsubstituted pyrene; or a salt thereof.

A further embodiment of the invention is a compound of formula (I), wherein: X is Se; Y is C; $R_1$ is —H, and R is substituted or unsubstituted heteroaryl; or a salt thereof.

A further embodiment of the invention is a compound of formula (I), wherein: X is Se; Y is C; $R_1$ is —H, and R is a substituted or unsubstituted heteroaryl selected from the group consisting of substituted or unsubstituted pyridine, substituted or unsubstituted quinoline, substituted or unsubstituted thiophene, substituted or unsubstituted pyrrole, substituted or unsubstituted furan, substituted or unsubstituted imidazole, substituted or unsubstituted oxazole, and substituted or unsubstituted thiazole; or a salt thereof.

A further embodiment of the invention is a compound of formula (I), wherein: X is Se; Y is C; $R_1$ is —H, and R is substituted or unsubstituted alkyl, or substituted or unsubstituted cycloalkyl; or a salt thereof.

A further embodiment of the invention is a compound of formula (I), wherein: X is Se; Y is C; $R_1$ is —H, and R is substituted or unsubstituted alkyl; or a salt thereof.

A further embodiment of the invention is a compound of formula (I), wherein: X is Se; Y is C; $R_1$ is —H, and R is a $C_1$-$C_{20}$ alkyl that is unsubstituted or substituted with one or more substituents selected from the group consisting of $C_1$-$C_6$ alkyl, —$OR_a$, —$SR_b$, —F, —Cl, —Br, —I, —CN, —$NO_2$, phenyl, pyridyl, —CHO, —$COOR_e$, —$CO(NR_fR_g)$; wherein each of $R_a$, $R_b$, $R_d$, $R_e$, $R_f$, and $R_g$ are independently selected from H or $C_1$-$C_6$ alkyl; or a salt thereof.

A further embodiment of the invention is a compound of formula (I), wherein: X is Se; Y is C; $R_1$ is —H, and R is selected from the group consisting of substituted or unsubstituted butyl, pentyl, hexyl, heptyl, octyl, decyl, and dodecyl; or a salt thereof.

A further embodiment of the invention is a compound of formula (I), wherein: X is Se; Y is C; $R_1$ is —H, and R is substituted or unsubstituted cycloalkyl; or a salt thereof.

A further embodiment of the invention is a compound of formula (I), wherein: X is Se; Y is C; $R_1$ is —H, and R is a monocyclic $C_3$-$C_{20}$ alkyl that is unsubstituted or substituted with one or more substituents selected from the group consisting of $C_1$-$C_6$ alkyl, —$OR_a$, —$SR_b$, —F, —Cl, —Br, —I, —CN, —$NO_2$, phenyl, pyridyl, —CHO, —$COOR_e$, —CO(NR$_f$R$_g$); wherein each of R$_a$, R$_b$, R$_c$, R$_d$, R$_e$, R$_f$, and R$_g$ are independently selected from H or C$_1$-C$_6$ alkyl; or a salt thereof.

A further embodiment of the invention is a compound of formula (I), wherein: X is Se; Y is C; R$_1$ is —H, and R is selected from the group consisting of substituted or unsubstituted cyclopropyl, cyclobutyl, cyclopentyl, cyclohexyl, cycloheptyl, cyclooctyl, cyclodecyl, and cyclododecyl; or a salt thereof.

A further embodiment of the invention is a compound of formula (I), wherein: X is Se; Y is C; R$_1$ is —H, and R is a bicyclic C$_6$-C$_{20}$ alkyl that is unsubstituted or substituted with one or more substituents selected from the group consisting of C$_1$-C$_6$ alkyl, —OR$_a$, —SR$_b$, —F, —Cl, —Br, —I, —CN, —NO$_2$, phenyl, pyridyl, —CHO, —COOR$_e$, —CO(NR$_f$R$_g$); wherein each of R$_a$, R$_b$, R$_c$, R$_d$, R$_e$, R$_f$, and R$_g$ are independently selected from H or C$_1$-C$_6$ alkyl; or a salt thereof.

A further embodiment of the invention is a compound of formula (I), wherein: X is Se; Y is C; R$_1$ is —H, and R is selected from decalin or norbornane; or a salt thereof.

A further embodiment of the invention is a compound of formula (I), wherein: X is Se; Y is C; R$_1$ is —H, and R is a tricyclic C$_3$-C$_{20}$ alkyl that is unsubstituted or substituted with one or more substituents selected from the group consisting of C$_1$-C$_6$ alkyl, —OR$_a$, —SR$_b$, —NR$_c$R$_d$, —F, —Cl, —Br, —I, —CN, —NO$_2$, phenyl, pyridyl, —CHO, —COOR$_e$, —CO(NR$_f$R$_g$); wherein each of R$_a$, R$_b$, R$_c$, R$_d$, R$_e$, R$_f$, and R$_g$ are independently selected from H or C$_1$-C$_6$ alkyl; or a salt thereof.

A further embodiment of the invention is a compound of formula (I), wherein: X is Se; Y is C; R$_1$ is —H, and R is adamantane; or a salt thereof.

A further embodiment of the invention is a compound of formula (I), wherein: X is S; Y is C; R$_1$ is —H, and R is substituted or unsubstituted aryl, substituted or unsubstituted heteroaryl, substituted or unsubstituted alkyl, or substituted or unsubstituted cycloalkyl; or a salt thereof.

A further embodiment of the invention is a compound of formula (I), wherein: X is S; Y is C; R$_1$ is —H, and R is substituted or unsubstituted aryl or substituted or unsubstituted heteroaryl; or a salt thereof.

A further embodiment of the invention is a compound of formula (I), wherein: X is S; Y is C; R$_1$ is —H, and R is substituted or unsubstituted aryl; or a salt thereof.

A further embodiment of the invention is a compound of formula (I), wherein: X is S; Y is C; R$_1$ is —H, and R is a substituted or unsubstituted aryl selected from the group consisting of substituted or unsubstituted phenyl, substituted or unsubstituted naphthalene, substituted or unsubstituted anthracene, substituted or unsubstituted phenanthrene, and substituted or unsubstituted pyrene; or a salt thereof.

A further embodiment of the invention is a compound of formula (I), wherein: X is S; Y is C; R$_1$ is —H, and R is substituted or unsubstituted heteroaryl; or a salt thereof.

A further embodiment of the invention is a compound of formula (I), wherein: X is S; Y is C; R$_1$ is —H, and R is a substituted or unsubstituted heteroaryl selected from the group consisting of substituted or unsubstituted pyridine, substituted or unsubstituted quinoline, substituted or unsubstituted thiophene, substituted or unsubstituted pyrrole, substituted or unsubstituted furan, substituted or unsubstituted imidazole, substituted or unsubstituted oxazole, and substituted or unsubstituted thiazole; or a salt thereof.

A further embodiment of the invention is a compound of formula (I), wherein: X is S; Y is C; R$_1$ is —H, and R is substituted or unsubstituted alkyl, or substituted or unsubstituted cycloalkyl; or a salt thereof.

A further embodiment of the invention is a compound of formula (I), wherein: X is S; Y is C; R$_1$ is —H, and R is substituted or unsubstituted alkyl; or a salt thereof.

A further embodiment of the invention is a compound of formula (I), wherein: X is S; Y is C; R$_1$ is —H, and R is a C$_1$-C$_{20}$ alkyl that is unsubstituted or substituted with one or more substituents selected from the group consisting of C$_1$-C$_6$ alkyl, —OR$_a$, —SR$_b$, —NR$_c$R$_d$, —Cl, —Br, —I, —CN, —NO$_2$, phenyl, pyridyl, —CHO, —COOR$_e$, —CO(NR$_f$R$_g$); wherein each of R$_a$, R$_b$, R$_d$, R$_e$, R$_f$, and R$_g$ are independently selected from H or C$_1$-C$_6$ alkyl; or a salt thereof.

A further embodiment of the invention is a compound of formula (I), wherein: X is S; Y is C; R$_1$ is —H, and R is selected from the group consisting of substituted or unsubstituted butyl, pentyl, hexyl, heptyl, octyl, decyl, and dodecyl; or a salt thereof.

A further embodiment of the invention is a compound of formula (I), wherein: X is S; Y is C; R$_1$ is —H, and R is substituted or unsubstituted cycloalkyl; or a salt thereof.

A further embodiment of the invention is a compound of formula (I), wherein: X is S; Y is C; R$_1$ is —H, and R is a monocyclic C$_3$-C$_{20}$ alkyl that is unsubstituted or substituted with one or more substituents selected from the group consisting of C$_1$-C$_6$ alkyl, —OR$_a$, —SR$_b$, —NR$_c$R$_d$, —F, —Cl, —Br, —I, —CN, —NO$_2$, phenyl, pyridyl, —CHO, —COOR$_e$, —CO(NR$_f$R$_g$); wherein each of R$_a$, R$_b$, R$_c$, R$_d$, R$_e$, R$_f$, and R$_g$ are independently selected from H or C$_1$-C$_6$ alkyl; or a salt thereof.

A further embodiment of the invention is a compound of formula (I), wherein: X is S; Y is C; R$_1$ is —H, and R is selected from the group consisting of substituted or unsubstituted cyclopropyl, cyclobutyl, cyclopentyl, cyclohexyl, cycloheptyl, cyclooctyl, cyclodecyl, and cyclododecyl; or a salt thereof.

A further embodiment of the invention is a compound of formula (I), wherein: X is S; Y is C; R$_1$ is —H, and R is a bicyclic C$_6$-C$_{20}$ alkyl that is unsubstituted or substituted with one or more substituents selected from the group consisting of C$_1$-C$_6$ alkyl, —OR$_a$, —SR$_b$, —NR$_c$R$_d$, —F, —Cl, —Br, —I, —CN, —NO$_2$, phenyl, pyridyl, —CHO, —COOR$_e$, —CO(NR$_f$R$_g$); wherein each of R$_a$, R$_b$, R$_c$, R$_d$, R$_e$, R$_f$, and R$_g$ are independently selected from H or C$_1$-C$_6$ alkyl; or a salt thereof.

A further embodiment of the invention is a compound of formula (I), wherein: X is S; Y is C; R$_1$ is —H, and R is selected from decalin or norbornane; or a salt thereof.

A further embodiment of the invention is a compound of formula (I), wherein: X is S; Y is C; R$_1$ is —H, and R is a tricyclic C$_3$-C$_{20}$ alkyl that is unsubstituted or substituted with one or more substituents selected from the group consisting of C$_1$-C$_6$ alkyl, —OR$_a$, —SR$_b$, —F, —Cl, —Br, —I, —CN, —NO$_2$, phenyl, pyridyl, —CHO, —COOR$_e$, —CO(NR$_f$R$_g$); wherein each of R$_a$, R$_b$, R$_c$, R$_d$, R$_e$, R$_f$, and R$_g$ are independently selected from H or C$_1$-C$_6$ alkyl; or a salt thereof.

A further embodiment of the invention is a compound of formula (I), wherein: X is S; Y is C; R$_1$ is —H, and R is adamantane; or a salt thereof.

A further embodiment of the invention is a compound of formula (I), wherein: X is S=O; Y is C; R$_1$ is —H, and R is substituted or unsubstituted alkyl, or substituted or unsubstituted cycloalkyl; or a salt thereof.

A further embodiment of the invention is a compound of formula (I), wherein: X is S=O; Y is C; R$_1$ is —H, and R is substituted or unsubstituted alkyl; or a salt thereof.

A further embodiment of the invention is a compound of formula (I), wherein: X is S=O; Y is C; $R_1$ is —H, and R is a $C_1$-$C_{20}$ alkyl that is unsubstituted or substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —CO($NR_fR_g$); wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a compound of formula (I), wherein: X is S=O; Y is C; $R_1$ is —H, and R is selected from the group consisting of substituted or unsubstituted butyl, pentyl, hexyl, heptyl, octyl, decyl, and dodecyl; or a salt thereof.

A further embodiment of the invention is a compound of formula (I), wherein: X is S=O; Y is C; $R_1$ is —H, and R is substituted or unsubstituted cycloalkyl; or a salt thereof.

A further embodiment of the invention is a compound of formula (I), wherein: X is S=O; Y is C; $R_1$ is —H, and R is a monocyclic $C_3$-$C_{20}$ alkyl that is unsubstituted or substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —CO($NR_fR_g$); wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a compound of formula (I), wherein: X is S=O; Y is C; $R_1$ is —H, and R is selected from the group consisting of substituted or unsubstituted cyclopropyl, cyclobutyl, cyclopentyl, cyclohexyl, cycloheptyl, cyclooctyl, cyclodecyl, and cyclododecyl; or a salt thereof.

A further embodiment of the invention is a compound of formula (I), wherein:

X=Se; Y=C; $R_1$=—H, and

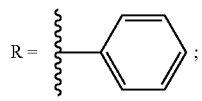 [SMILES: *c1ccccc1];

X=Se; Y=C; $R_1$=—H, and

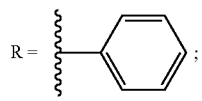;

X=Se; Y=C; $R_1$=—H, and

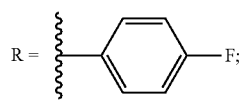;

X=Se; Y=C; $R_1$=—H, and

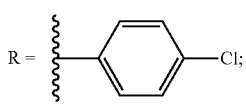;

X=Se; Y=C; $R_1$=—H, and

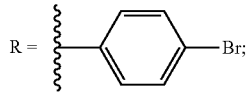 [SMILES: *c1ccc(Br)cc1]

X=Se; Y=C; $R_1$=—H, and

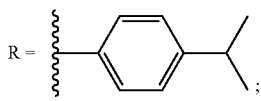;

X=Se; Y=C; $R_1$=—H, and

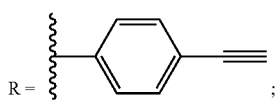;

X=Se; Y=C; $R_1$=—H, and

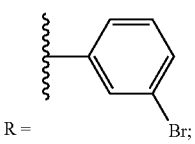 [SMILES: *c1cccc(Br)c1]

X=Se; Y=C; $R_1$=—H, and

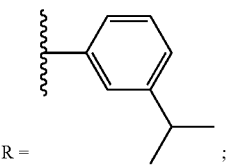 [SMILES: *c1cccc(C(C)C)c1 ; ";"];

X=Se; Y=C; $R_1$=—H, and

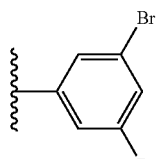;

X=Se; Y=C; $R_1$=—H, and

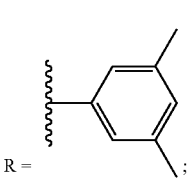 [SMILES: *c1cc(C)cc(C)c1];

X=Se; Y=C; R₁=—H, and
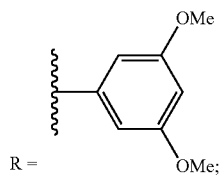 [SMILES: *c1cc(OC)cc(OC)c1]
X=Se; Y=C; R₁=—H, and
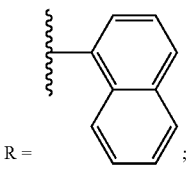
X=Se; Y=C; R₁=—H, and
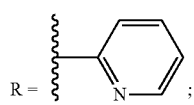 [SMILES: *c1ccccn1]
X=Se; Y=C; R₁=—H, and
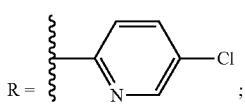
X=Se; Y=C; R₁=—H, and
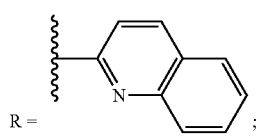
X=Se; Y=C; R₁=—H, and
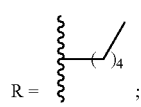
X=Se; Y=C; R₁=—H, and
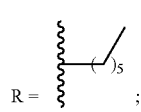
X=Se; Y=C; R₁=—H, and
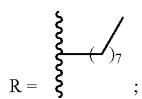
X=Se; Y=C; R₁=—H, and
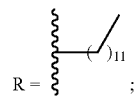
X=Se; Y=C; R₁=—H, and
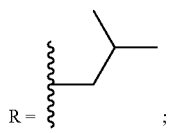
X=Se; Y=C; R₁=—H, and
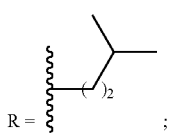
X=Se; Y=C; R₁=—H, and
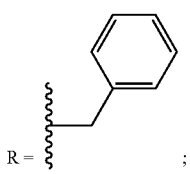 [SMILES: *Cc1ccccc1]
X=Se; Y=C; R₁=—H, and
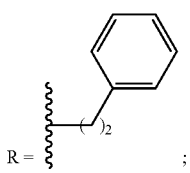

X=Se; Y=C; $R_1$=—H, and

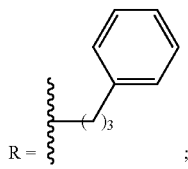

X=Se; Y=C; $R_1$=—H, and

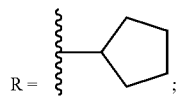

X=Se; Y=C; $R_1$=—H, and

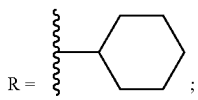

X=Se; Y=C; $R_1$=—H, and

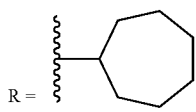

X=Se; Y=C; $R_1$=—H, and

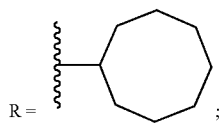

X=Se; Y=C; $R_1$=—H, and

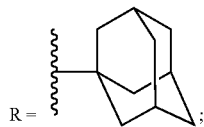

X=Se=O; Y=C; $R_1$=—H, and

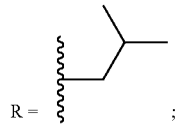 [SMILES: *CC(C)C]

X=Se=O; Y=C; $R_1$=—H, and or

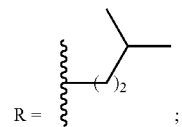

X=Se=O; Y=C; $R_1$=—H, and

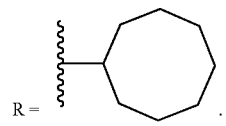

A further embodiment of the invention is a compound of formula (I), wherein: X is S; Y is N; $R_1$ is selected from the group consisting of —H, —OH, —NH$_2$, —OR$_b$, CF$_3$, NO$_2$, or CN; R is selected from the group consisting of substituted alkyl, unsubstituted alkyl, and OR$_a$; R$_a$ is selected from the group consisting of linear C$_{1-16}$ alkyl groups, branched C$_{1-16}$ alkyl groups, or linear pegylated C$_{4-16}$ alkyl groups; or a salt thereof.

A further embodiment of the invention is a compound of formula (I), wherein: X is S; Y is N; $R_1$ is selected from the group consisting of —H, —OH, —NH$_2$, —OMe, —OEt, OPr, OiPr, CF$_3$, NO$_2$, or CN; and R is selected from methyl, ethyl, propyl, or isopropyl; or a salt thereof.

A further embodiment of the invention is a compound of formula (I), wherein: X is S; Y is N; $R_1$ is selected from the group consisting of —H, —OH, —NH$_2$, —OMe, —OEt, OPr, OiPr, CF$_3$, NO$_2$, or CN; and R is —O—CH$_2$—CH$_2$—O—CH$_2$; or a salt thereof.

A further embodiment of the invention is a compound of formula (I), wherein: X is S; Y is O; $R_1$ is selected from the group consisting of —H, —OH, —NH$_2$, —OR$_b$, CF$_3$, NO$_2$, or CN; R is selected from the group consisting of substituted alkyl, unsubstituted alkyl, and OR$_a$; R$_a$ is selected from the group consisting of linear C$_{1-16}$ alkyl groups, branched C$_{1-16}$ alkyl groups, or linear pegylated C$_{4-16}$ alkyl groups; or a salt thereof.

A further embodiment of the invention is a compound of formula (I), wherein: X is S; Y is O; $R_1$ is selected from the group consisting of —H, —OH, —NH$_2$, —OMe, —OEt, OPr, OiPr, CF$_3$, NO$_2$, or CN; and R is selected from methyl, ethyl, propyl, or isopropyl; or a salt thereof.

A further embodiment of the invention is a compound of formula (I), wherein: X is S; Y is O; $R_1$ is selected from the group consisting of —H, —OH, —NH$_2$, —OMe, —OEt, OPr, OiPr, CF$_3$, NO$_2$, or CN; and R is —O—CH$_2$—CH$_2$—O—CH$_2$; or a salt thereof.

Another aspect of the invention is a new pharmaceutical composition comprising a therapeutically effective amount of at least one compound of formula (I) or a salt thereof and at least one pharmaceutically acceptable excipient. The compounds of the invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3.sup.rd Ed.), American Pharmaceutical Association, Washington, 1999.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. For example, pharmaceutical compounds of formula (I) or salts thereof may be present in pharmaceutical compositions in an amount of 1 µg to 1000 mg, 1 µg to 1 mg, 1 µg to 500 1 µg to 250 or 1 µg to 100 µg. Pharmaceutical compounds of formula (I) or salts thereof may also be present in pharmaceutical compositions in an amount of 1 mg to 1000 mg, 1 mg to 500 mg, 1 mg to 250 mg, 1 mg to 100 mg, .

In many instances, the administration of the compound will be repeated a plurality of times in a day. Multiple doses per day typically may be used to increase the total daily dose, if desired.

Another aspect of the invention is a new pharmaceutical composition comprising a therapeutically effective amount of at least one compound of formula (I) or a salt thereof and at least one pharmaceutically acceptable excipient, wherein the pharmaceutical composition is administered once per day, twice per day, or three times per day.

A further embodiment of the invention is a new pharmaceutical composition comprising a therapeutically effective amount of at least one compound of formula (I) or a salt thereof and at least one pharmaceutically acceptable excipient, wherein the pharmaceutical composition is in the form of a solution, suspension, gel, emulsion, solid, or powder. Any of these forms may be used for oral administration, topical administration, or parenteral administration, intranasal administration, or rectal administration.

Another aspect of the invention is a new agricultural composition comprising a therapeutically effective amount of at least one compound of formula (I) or a salt thereof and at least one agriculturally acceptable excipient. The compounds of the invention may be administered by any suitable route, preferably in the form of an agricultural composition adapted to such a route, and in a dose effective for the treatment intended. The active compounds and compositions, for example, may be administered to plant parts or to the soil or other growth medium surrounding the roots of the plants or to the seed of the plant before it is sown using standard agricultural techniques (such as spraying).

Agricultural compositions of the invention may be prepared by any of the well-known techniques of agricultural practices, such as effective formulation and administration procedures.

The dosage regimen for the compounds and/or compositions containing the compounds is based on a variety of factors, including the type of agricultural crop, the weather, and the season; the severity of the condition; the route of administration; and the activity of the particular compound employed. Thus the dosage regimen may vary widely. Dosage levels of the order from about 0.01 mg to about 100 mg per kilogram of plant weight per day are useful in the treatment of the above-indicated conditions.

Yet another aspect of the invention is a new method of treating an infection caused by a fungal species, comprising administering to a subject in need thereof a therapeutically effective amount of a compound of formula (I):

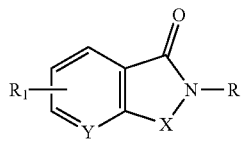

(I)

wherein
X may be Se, S, or S=O;
Y may be C, N, or O;
R may be substituted or unsubstituted aryl, substituted or unsubstituted heteroaryl, substituted or unsubstituted alkyl, substituted or unsubstituted cycloalkyl, or $OR_a$;
$R_1$ may be —H, —OH, —$NH_2$, $OR_b$, $CF_3$, $NO_2$, or CN;
$R_a$ may be linear or branched $C_{1-16}$ alkyl groups or linear pegylated $C_{4-16}$ alkyl groups; and
$R_b$ may be linear or branched $C_{1-16}$ alkyl groups; or a salt thereof.

In one embodiment of the invention, subject in need of treatment of an infection caused by a fungal species with a therapeutically effective amount of a compound of formula (I) may be an animal. Examples of animals that may be treated according to the invention include invertebrates and vertebrates. Examples of invertebrates that may be treated according to the invention include *Apis mellifera, Drosophila melanogaster,* and *Caenorhabditis elegans.* Examples of vertebrates that may be treated according to the invention include fish (e.g., zebrafish), amphibians (e.g., *Xenopus laevis* and *Xenopus tropicalis*), and mammals.

In one embodiment of the invention, subject in need of treatment of an infection caused by a fungal species with a therapeutically effective amount of a compound of formula (I) may be a mammal. Examples of mammals that may be treated according to the invention include humans, primates, horses, sheep, pigs, cows, mice, rats, rabbits, dogs, and cats.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is substituted or unsubstituted aryl, substituted or unsubstituted heteroaryl, substituted or unsubstituted alkyl, or substituted or unsubstituted cycloalkyl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is substituted or unsubstituted aryl or substituted or unsubstituted heteroaryl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is substituted or unsubstituted aryl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is a substituted or unsubstituted aryl selected from the group consisting of substituted or unsubstituted phenyl, substituted or unsubstituted naphthalene, substituted or unsubstituted anthracene, substituted or unsubstituted phenanthrene, and substituted or unsubstituted pyrene; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is substituted or unsubstituted heteroaryl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is a substituted or unsubstituted heteroaryl selected from the group consisting of substituted or unsubstituted pyridine, substituted or unsubstituted quinoline, substituted or unsubstituted thiophene, substituted or unsubstituted pyrrole, substituted or unsubstituted furan, substituted or unsubstituted imidazole, substituted or unsubstituted oxazole, and substituted or unsubstituted thiazole; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is substituted or unsubstituted alkyl, or substituted or unsubstituted cycloalkyl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is substituted or unsubstituted alkyl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is a $C_1$-$C_{20}$ alkyl that is unsubstituted or substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —$CO(NR_fR_g)$; wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is selected from the group consisting of substituted or unsubstituted butyl, pentyl, hexyl, heptyl, octyl, decyl, and dodecyl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is substituted or unsubstituted cycloalkyl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is a monocyclic $C_3$-$C_{20}$ alkyl that is unsubstituted or substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —$CO(NR_fR_g)$; wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is selected from the group consisting of substituted or unsubstituted cyclopropyl, cyclobutyl, cyclopentyl, cyclohexyl, cycloheptyl, cyclooctyl, cyclodecyl, and cyclododecyl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is a bicyclic $C_6$-$C_{20}$ alkyl that is unsubstituted or substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —$CO(NR_fR_g)$; wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is selected from decalin or norbornane; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is a tricyclic $C_3$-$C_{20}$ alkyl that is unsubstituted or substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —$CO(NR_fR_g)$; wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a new method of treating an infection caused by a fungal species, comprising administering to a subject in need thereof a therapeutically effective amount of a compound of formula (I), wherein: X is Se; Y is C; $R_1$ is —H, and R is adamantane; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is substituted or unsubstituted aryl, substituted or unsubstituted heteroaryl, substituted or unsubstituted alkyl, or substituted or unsubstituted cycloalkyl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is substituted or unsubstituted aryl or substituted or unsubstituted heteroaryl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is substituted or unsubstituted aryl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is a substituted or unsubstituted aryl selected from the group consisting of substituted or unsubstituted phenyl, substituted or unsubstituted naphthalene, substituted or unsubstituted anthracene, substituted or unsubstituted phenanthrene, and substituted or unsubstituted pyrene; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is substituted or unsubstituted heteroaryl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is a substituted or unsubstituted heteroaryl selected from the group consisting of substituted or unsubstituted pyridine, substituted or unsubstituted quinoline, substituted or unsubstituted thiophene, substituted or unsubstituted pyrrole, substituted or unsubstituted furan, substituted or unsubstituted imidazole, substituted or unsubstituted oxazole, and substituted or unsubstituted thiazole; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is substituted or unsubstituted alkyl, or substituted or unsubstituted cycloalkyl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is substituted or unsubstituted alkyl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is a $C_1$-$C_{20}$ alkyl that is unsubstituted or substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —$CO(NR_fR_g)$; wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is selected from the group consisting of substituted or unsubstituted butyl, pentyl, hexyl, heptyl, octyl, decyl, and dodecyl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is substituted or unsubstituted cycloalkyl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is a monocyclic $C_3$-$C_{20}$ alkyl that is unsubstituted or substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —$CO(NR_fR_g)$; wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is selected from the group consisting of substituted or unsubstituted cyclopropyl, cyclobutyl, cyclopentyl, cyclohexyl, cycloheptyl, cyclooctyl, cyclodecyl, and cyclododecyl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is a bicyclic $C_6$-$C_{20}$ alkyl that is unsubstituted or substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —$CO(NR_fR_g)$; wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is selected from decalin or norbornane; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is a tricyclic $C_3$-$C_{20}$ alkyl that is unsubstituted or substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —$CO(NR_fR_g)$; wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a new method of treating an infection caused by a fungal species, comprising administering to a subject in need thereof a therapeutically effective amount of a compound of formula (I), wherein: X is S; Y is C; $R_1$ is —H, and R is adamantane; or a salt thereof.

A further embodiment of the invention is a new method of treating an infection caused by a fungal species, comprising administering to a subject in need thereof a therapeutically effective amount of a compound of formula (I), wherein: X is S=O; Y is C; $R_1$ is —H, and R is substituted or unsubstituted alkyl, or substituted or unsubstituted cycloalkyl; or a salt thereof.

A further embodiment of the invention is a new method of treating an infection caused by a fungal species, comprising administering to a subject in need thereof a therapeutically effective amount of a compound of formula (I), wherein: X is S=O; Y is C; $R_1$ is —H, and R is substituted or unsubstituted alkyl; or a salt thereof.

A further embodiment of the invention is a new method of treating an infection caused by a fungal species, comprising administering to a subject in need thereof a therapeutically effective amount of a compound of formula (I), wherein: X is S=O; Y is C; $R_1$ is —H, and R is a $C_1$-$C_{20}$ alkyl that is unsubstituted or substituted with one or more substituents selected from the group consisting of $C_1$-$C_6$ alkyl, —$OR_a$, —$SR_b$, —$NR_cR_d$, —F, —Cl, —Br, —I, —CN, —$NO_2$, phenyl, pyridyl, —CHO, —$COOR_e$, —$CO(NR_fR_g)$; wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a new method of treating an infection caused by a fungal species, comprising administering to a subject in need thereof a therapeutically effective amount of a compound of formula (I), wherein: X is S=O; Y is C; $R_1$ is —H, and R is selected from the group consisting of substituted or unsubstituted butyl, pentyl, hexyl, heptyl, octyl, decyl, and dodecyl; or a salt thereof.

A further embodiment of the invention is a new method of treating an infection caused by a fungal species, comprising administering to a subject in need thereof a therapeutically effective amount of a compound of formula (I), wherein: X is S=O; Y is C; $R_1$ is —H, and R is substituted or unsubstituted cycloalkyl; or a salt thereof.

A further embodiment of the invention is a new method of treating an infection caused by a fungal species, comprising administering to a subject in need thereof a therapeutically effective amount of a compound of formula (I), wherein: X is S=O; Y is C; $R_1$ is —H, and R is a monocyclic $C_3$-$C_{20}$ alkyl that is unsubstituted or substituted with one or more substituents selected from the group consisting of $C_1$-$C_6$ alkyl, —$OR_a$, —$SR_b$, —F, —Cl, —Br, —I, —CN, —$NO_2$, phenyl, pyridyl, —CHO, —$COOR_e$, —$CO(NR_fR_g)$; wherein each of $R_a$, $R_b$, $R_c$, $R_d$, $R_e$, $R_f$, and $R_g$ are independently selected from H or $C_1$-$C_6$ alkyl; or a salt thereof.

A further embodiment of the invention is a new method of treating an infection caused by a fungal species, comprising administering to a subject in need thereof a therapeutically effective amount of a compound of formula (I), wherein: X is S=O; Y is C; R$_1$ is —H, and R is selected from the group consisting of substituted or unsubstituted cyclopropyl, cyclobutyl, cyclopentyl, cyclohexyl, cycloheptyl, cyclooctyl, cyclodecyl, and cyclododecyl; or a salt thereof.

A further embodiment of the invention is a new method of treating an infection caused by a fungal species, comprising administering to a subject in need thereof a therapeutically effective amount of a compound of formula (I), wherein:

X=Se; Y=C; R$_1$=—H, and

R = [phenyl];

X=S; Y=C; R$_1$=—H, and

R = [phenyl];

X=S; Y=C; R$_1$=—H, and

R = [4-fluorophenyl]—F;

X=S; Y=C; R$_1$=—H, and

R = [4-chlorophenyl]—Cl;

X=S; Y=C; R$_1$=—H, and

R = [4-bromophenyl]—Br;

X=S; Y=C; R$_1$=—H, and

R = [4-isopropylphenyl];

X=S; Y=C; R$_1$=—H, and

R = [4-ethynylphenyl];

X=S; Y=C; R$_1$=—H, and

R = [3-bromophenyl]Br;

X=S; Y=C; R$_1$=—H, and

R = [3-isopropylphenyl];

X=S; Y=C; R$_1$=—H, and

R = [3,5-dibromophenyl]Br, Br;

X=S; Y=C; R$_1$=—H, and

R = [3,5-dimethylphenyl];

X=S; Y=C; R$_1$=—H, and

R = [3,5-dimethoxyphenyl]OMe, OMe;

X=S; Y=C; R₁=—H, and
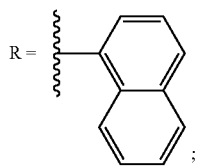 [SMILES: *c1cccc2ccccc12]
X=S; Y=C; R₁=—H, and
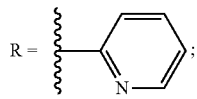
X=S; Y=C; R₁=—H, and
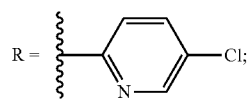
X=S; Y=C; R₁=—H, and
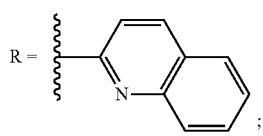
X=S; Y=C; R₁=—H, and
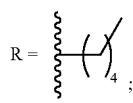
X=S; Y=C; R₁=—H, and
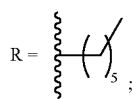
X=S; Y=C; R₁=—H, and
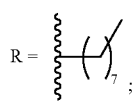
X=S; Y=C; R₁=—H, and
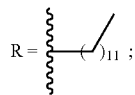
X=S; Y=C; R₁=—H, and
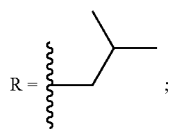
X=S; Y=C; R₁=—H, and
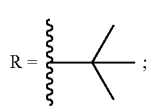
X=S; Y=C; R₁=—H, and
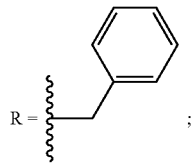
X=S; Y=C; R₁=—H, and
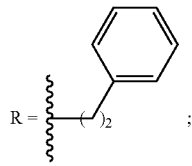
X=S; Y=C; R₁=—H, and
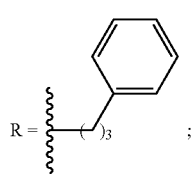
X=S; Y=C; R₁=—H, and
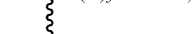

X=S; Y=C; R$_1$=—H, and

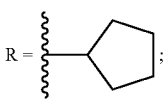

X=S; Y=C; R$_1$=—H, and

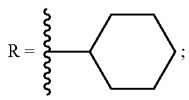

X=S; Y=C; R$_1$=—H, and

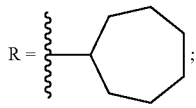

X=S; Y=C; R$_1$=—H, and

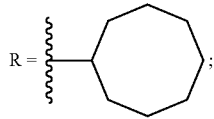

X=S; Y=C; R$_1$=—H, and

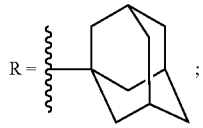

X=S=O; Y=C; R$_1$=—H, and

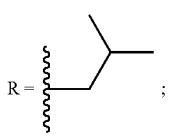

X=S=O; Y=C; R$_1$=—H, and or

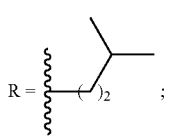

X=S=O; Y=C; R$_1$=—H, and

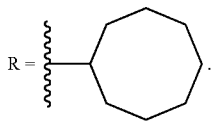 [SMILES: *C1CCCCCCC1]

A further embodiment of the invention is a method of treating an infection caused by a fungal species, comprising administering to a subject in need thereof a therapeutically effective amount of a compound of formula (I) or a salt thereof, wherein the fungal species is a *Candida, Aspergillus, Trichophyton, Fusarium, Microsporum, Blumeria, Podosphaera, Sphaerotheca, Phakopsora, Puccinia, Uromyces, Peronospora, Phytophthora, Plasmopara, Pythium, Alternaria, Cercospora, Cladiosporium, Colletotrichum, Cycloconium, Cochliobolus, Gloeosporium, Glomerella, Guignardia, Leptosphaeria, Magnaporthe, Botrytis, Penicillium, Sclerotinia, Verticillium, Rhizoctonia, Sclerotium, Nectria, Monilinia*, and *Helminthosporium* species.

A further embodiment of the invention is a method of treating an infection caused by a fungal species, comprising administering to a subject in need thereof a therapeutically effective amount of a compound of formula (I) or a salt thereof, wherein the fungal species is selected from the group consisting of *Candida albicans, Candida glabrata, Candida krusei,* or *Candida parapsilosis.*

A further embodiment of the invention is a method of treating an infection caused by a fungal species, comprising administering to a subject in need thereof a therapeutically effective amount of a compound of formula (I) or a salt thereof, wherein the fungal species is selected from the group consisting of *Aspergillus flavus, Aspergillus nidulans,* and *Aspergillus terreus.*

A further embodiment of the invention is a method of treating an infection caused by a fungal species, comprising administering to a subject in need thereof a therapeutically effective amount of a compound of formula (I) or a salt thereof, wherein the fungal species is selected from the group consisting of *Trichophyton rubrum, Trichophyton tonsurans,* and *Trichophyton interdigitale.*

A further embodiment of the invention is a method of treating an infection caused by a fungal species, comprising administering to a subject in need thereof a therapeutically effective amount of a compound of formula (I) or a salt thereof, wherein the fungal species is selected from the group consisting of *Microsporum canis* and *Microsporum gypseum.*

In one embodiment of the invention, the subject in need of treatment of an infection caused by a fungal species with a therapeutically effective amount of a compound of formula (I) may be a mammal. Examples of mammals that may be treated according to the invention include humans, primates, horses, sheep, pigs, cows, mice, rats, rabbits, dogs, and cats.

In another embodiment of the invention, the subject in need of treatment of an infection caused by a fungal species with a therapeutically effective amount of a compound of formula (I) may be an agricultural crop. Examples of agricultural crops that may be treated according to the invention include grains, vegetables, and fruit.

A further embodiment of the invention is a method of treating powdery mildew diseases comprising administering to a subject in need thereof a therapeutically effective amount of a compound of formula (I) or a salt thereof, wherein the powdery mildew diseases include (1) *Blumeria* diseases caused, for example, by *Blumeria graminis*; (2) Podosphaera diseases caused, for example, by *Podosphaera*

*leucotricha*; and (3) Sphaerotheca diseases caused, for example, by *Sphaerotheca fuliginea*.

A further embodiment of the invention is a method of treating rust diseases comprising administering to a subject in need thereof a therapeutically effective amount of a compound of formula (I) or a salt thereof, wherein the rust diseases include (1) *Phakopsora* diseases caused, for example, by *Phakopsora pachyrhizi* and *Phakopsora meibomiae*; (2) *Puccinia* diseases caused, for example, by *Puccinia recondite*, and *Puccinia triticina*; and (3) *Uromyces* diseases caused, for example, by *Uromyces appendiculatus*.

A further embodiment of the invention is a method of treating oomycete diseases comprising administering to a subject in need thereof a therapeutically effective amount of a compound of formula (I) or a salt thereof, wherein the oomycete diseases include (1) *Peronospora* diseases caused, for example, by *Peronospora pisi* and *Peronospora brassicae*; (2) Phytophthora diseases caused, for example, by *Phytophthora infestans*; (3) *Plasmopara* diseases caused, for example, by *Plasmopara viticola*; and (4) Pythium diseases caused, for example, by *Pythium ultimum*.

A further embodiment of the invention is a method of treating leafspot, leaf blotch and leaf blight diseases comprising administering to a subject in need thereof a therapeutically effective amount of a compound of formula (I) or a salt thereof, wherein the leafspot, leaf blotch, and leaf blight diseases include (1) *Alternaria* diseases caused, for example, by *Alternaria solani*; (2) Cercospora diseases caused, for example, by *Cercospora beticola*; (3) *Cladiosporium* diseases caused, for example, by *Cladiosporium cucumerinum*; (4) *Colletotrichum* diseases caused, for example, by *Colletotrichum lindemuthianum*; (5) *Cycloconium* diseases caused, for example, by *Cycloconium oleaginum*; (6) *Cochliobolus* diseases caused, for example, by *Cochliobolus sativus*; (7) *Gloeosporium* diseases caused, for example, by *Gloeosporium laeticolor*; (8) *Glomerella* diseases caused, for example, by *Glomerella cingulata*; (9) *Guignardia* diseases caused, for example, by *Guignardia bidwellii*; (10) *Leptosphaeria* diseases caused, for example, by *Leptosphaeria maculans*; and (11) *Magnaporthe* diseases caused, for example, by *Magnaporthe grisea*.

A further embodiment of the invention is a method of treating fruit rot and mold diseases comprising administering to a subject in need thereof a therapeutically effective amount of a compound of formula (I) or a salt thereof, wherein the fruit rot and mold diseases include (1) *Aspergillus* diseases caused, for example, by *Aspergillus flavus*; (2) *Botrytis* diseases caused, for example, by *Botrytis cinerea*; (3) *Penicillium* diseases caused, for example, by *Penicillium expansum* and *Penicillium purpurogenum*; (4) *Sclerotinia* diseases caused, for example, by *Sclerotinia sclerotiorum*; and (5) *Verticillium* diseases caused, for example, by *Verticillium alboatrum*.

A further embodiment of the invention is a method of treating seed- and soil-borne decay, mold, wilt, rot, and damping-off diseases comprising administering to a subject in need thereof a therapeutically effective amount of a compound of formula (I) or a salt thereof, wherein the seed- and soil-borne decay, mold, wilt, rot, and damping-off diseases include (1) *Fusarium* diseases caused, for example, by *Fusarium culmorum*; (2) *Phytophthora* diseases caused, for example, by *Phytophthora cactorum*; (3) *Rhizoctonia* diseases caused, for example, by *Rhizoctonia solani*; and (4) *Sclerotium* diseases caused, for example, by *Sclerotium rolfsii*;

A further embodiment of the invention is a method of treating canker, broom and dieback diseases comprising administering to a subject in need thereof a therapeutically effective amount of a compound of formula (I) or a salt thereof, wherein the canker, broom and dieback diseases include *Nectria* diseases caused, for example, by *Nectria galligena*.

A further embodiment of the invention is a method of treating Blight Diseases comprising administering to a subject in need thereof a therapeutically effective amount of a compound of formula (I) or a salt thereof, wherein the blight diseases include *Monilinia* diseases caused, for example, by *Monilinia laxa*.

A further embodiment of the invention is a method of treating diseases of flowers and seeds comprising administering to a subject in need thereof a therapeutically effective amount of a compound of formula (I) or a salt thereof, wherein the diseases of flowers and seeds include (1) *Botrytis* diseases caused, for example, by *Botrytis cinerea*; and (2) *Helminthosporium* diseases caused, for example, by *Helminthosporium solani*.

The compounds of the invention can be used, alone or in combination with other therapeutic agents, in the treatment of various conditions or disease states. The compound(s) of the invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The invention includes the use of a combination of a compound of Formula (I) and one or more additional pharmaceutically active agent(s). If a combination of active agents is administered, then they may be administered sequentially or simultaneously, in separate dosage forms or combined in a single dosage form. Accordingly, the invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compounds of this invention may also be used in conjunction with other pharmaceutical agents for the treatment of the diseases, conditions and/or disorders described herein. Therefore, methods of treatment that include administering compounds of the invention in combination with other pharmaceutical agents are also provided. Suitable pharmaceutical agents that may be used in combination with the compounds of the invention include, without limitation: include azoles (e.g., fluconazole (FLC), itraconazole (ITC), posaconazole (POS), and voriconazole (VOR)), polyenes (e.g., amphotericin B (AmB), nystatin (NYS), and candicidin (CAN)), allylamines (e.g., butenafine, naftifine, and terbinafine), and echinocandins (e.g., micafungin, caspofungin, and anidulafungin).

Pharmaceutical compositions of the invention may contain pharmaceutical excipients including antiadherents, binders, disintegrants, fillers, diluents, glidants, lubricants, preservatives, and the like, which are known to a person skilled in the art.

Suitable pharmaceutically acceptable excipients include, but are not limited to, antioxidants, preservatives, coloring, flavoring and diluting agents, emulsifying agents, suspending agents, solvents, fillers, bulking agents, buffers, delivery vehicles, diluents, and/or pharmaceutical adjuvants.

EXAMPLES

Ebsulfur and its analogues were prepared according to the procedures disclosed in Ngo, H. X. et al. (2016) Development of ebsulfur analogues as potent antibacterials against methicillin-resistant *Staphylococcus aureus. Bioorg. Med. Chem.* doi: 10.1016/j.bmc.2016.03.060, which is incorporated herein by reference in its entirety.

The antifungal agents amphotericin B (AmB), fluconazole (FLC), itraconazole (ITC), posaconazole (POS), and voriconazole (VOR) were obtained from AK Scientific (Union City, Calif., USA) and used without further purification. AmB, FLC, ITC, POS, and VOR were dissolved in DMSO at a final concentration of 5 mg/mL. All these antifungal agent stocks were stored at −20° C.

Compounds 1-4n, which feature ebselen (1) and ebsulfur (2a) as the main scaffolds, were evaluated. From the ebsulfur scaffold, the library was further organized into three subseries: analogues with aromatic substituents (2 series, 2a-o), analogues with aliphatic substituents (3 series, 3a-o), and oxidized sulfoxide analogues (4 series, 4e, 4f, and 4n):

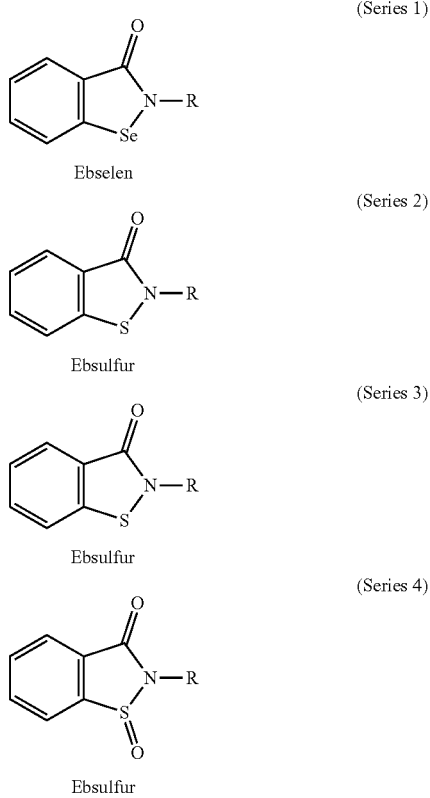

Ebselen (Series 1)

Ebsulfur (Series 2)

Ebsulfur (Series 3)

Ebsulfur (Series 4)

Fungal MIC determination experiments were performed using untreated 96-well plates (Corning). Cells were counted either by using a hemocytometer (Haussser Scientific, Horsham, Pa., USA) or by measuring optical density at attenuance of 600 nm ($OD_{600}$) by using a Genesys 20 spectrophotometer (Thermo Scientific, Waltham, Mass., USA). Spectrophotometric and colorimetric measurements in 96-well plates were performed using a SpectraMax M5 spectrometer (Molecular Devices, Sunnyvale, Calif., USA).

Yeast strains *Candida albicans* ATCC 10231 (strain A), *C. albicans* ATCC 64124 (strain B), and *C. albicans* ATCC MYA-2876(S) (strain C) were kindly provided by Dr. Jon Y. Takemoto (Utah State University, Logan, UT, USA). *C. albicans* ATCC MYA-90819(R) (strain D), *C. albicans* ATCC MYA-2310(S) (strain E), *C. albicans* ATCC 1237(R) (strain F), *C. albicans* ATCC MYA-1003(R) (strain G), *Candida glabrata* ATCC 2001 (strain H), *Candida krusei* ATCC 6258 (strain I), and *Candida parapsilosis* ATCC 22019 (strain J) were obtained from the American Type Culture Collection (ATCC, Manassas, Va., USA). The (S) and (R) indicate that ATCC reports these strains to be susceptible (S) and resistant (R) to ITC and FLC. The filamentous fungal strains *Aspergillus flavus* ATCC MYA-3631 (strain K), and *Aspergillus terreus* ATCC MYA-3633 (strain M) were also obtained from the American Type Culture Collection (ATCC, Manassas, Va., USA). *Aspergillus nidulans* ATCC 38163 (strain L) was kindly provided by Dr. Jon S. Thorson (University of Kentucky, Lexington, Ky., USA), respectively. Yeast strains were cultured at 35° C. Filamentous fungal strains were cultured at 25° C. and the spores were harvested. All fungal strains were cultured in RPMI 1640 medium (catalog # R6504, Sigma-Aldrich Chemical Co., St. Louis, Mo.) buffered to pH 7.0 with 0.165 M morpholinepropanesulfonic acid (MOPS) buffer (Sigma-Aldrich Chemical Co.).

The human embryonic kidney cell line HEK-293 (ATCC CRL-1573) and the murine macrophage cell line J774A.1 (ATCC TIB-67) were kindly provided by Dr. Matthew S. Gentry and Dr. David J. Feola (University of Kentucky, Lexington, Ky., USA), respectively. The HEK-293 cell line was grown in Dulbecco's Modified Eagle's Medium (DMEM) (ATCC, Manassas, Va., USA) with 10% fetal bovine serum (FBS) (ATCC, Manassas, Va., USA) and 1% Pen/Strep (ATCC, Manassas, Va., USA). The J774A.1 cell line was grown under the same conditions, except that the medium used was a different type of DMEM (catalog #30-2002, ATCC, Manassas, Va., USA). The HEK-293 cell line was passaged by trypsinization with 0.05%-trypsin-0.53 mM EDTA (ATCC, Manassas, Va., USA). The J774A.1 cell line was passaged mechanically by cell scrapers (ATCC, Manassas, Va., USA). Cell confluency was observed by using a Nikon Eclipse TS100 microscope (Minato, Tokyo, Japan).

Example 1

Antifungal Activity

The MIC values against fungal strains were determined based on a previously published protocol. MIC values for ebsulfur (2a) analogues against fungal cells were evaluated in 96-well plates as described in the CLSI document M27-A3 with minor modifications. Some of the fungal strains, such as *C. albicans* ATCC 64124 (strain B) tend to produce pseudohyphae (filaments) in RPMI 1640 medium, which was found to hinder cell counting when using a hemocytometer. Therefore, potato dextrose broth (PDB) was used to grow the yeast inocula of all strains tested, which were later diluted in RPMI 1640 medium to perform determination of MIC values. Minor modifications included growing yeast cells in PDB for 24-48 h at 35° C. at 200 rpm, diluting in RPMI 1640 medium to a concentration of $1 \times 10^6$ cells/mL (as determined by using a hemocytometer or an $OD_{600}$ of 0.12) and using a final inoculum size of 5×10³ CFU/mL for all the assays. The tested compounds (10 mg/mL) were diluted to the working stocks (500 µg/mL) by addition of DMSO. Two-fold serial dilution of the working stocks was prepared by addition of RPMI 1640 medium (100 µL) and cell suspension (100 µL) to 96-well microtiter plate to achieve final drug and inoculum concentrations ranging from 12.5-0.02 µg/mL and 5×10³ CFU/mL, respectively. Plates were incubated for 48 h at 35° C.

The MIC values for all tested compounds studied were defined as the lowest drug concentration that inhibits the visible growth of fungal strains after a 48-h incubation period. MIC assays for the spore-forming filamentous fungi, such as strain A. flavus ATCC MYA-3631 (strain K), were performed in a similar fashion. The filamentous fungal strains were first cultured at 25° C. on potato dextrose agar (PDA) plates for 3-5 days or until confluent. Spores were collected by washing the surface of the agar plates with dd H₂O (5 mL) and then isolated the spores by gravity filtration (the spores are H₂O soluble). The spores were then counted by using a hemocytometer and added to the MIC assays to achieve a final concentration of 5×10³ cells/mL. Researchers working with spores should wear a facemask to prevent spore inhalation. These MIC data are presented in Tables 1.

Compounds of formula (I) were evaluated for whole-cell activity against a panel of clinically relevant fungal strains (Table 1). The ebsulfur scaffold was further organized into three sub-series: (1) analogues with aromatic substituents (2 series, 2a-o), including mono- and disubstituted phenyl rings (2a-k), naphthyl (2l), and nitrogen-containing aromatic heterocycles (2m-o); (2) analogues with aliphatic substituents (3 series, 3a-o), including linear alkyl chains (3a-d), branched alkyl chains (3e-g), alkyl with terminal phenyl ring (3h-j), aliphatic rings (3k-n), and adamantyl (3o); and (3) oxidized sulfoxide analogues (4 series, 4e, 4f, and 4n). Commercially available AmB, FLC, ITC, POS, and VOR were used as positive controls.

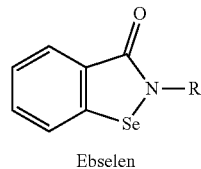
Ebselen (Series 1)

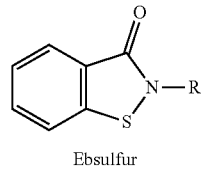
Ebsulfur (Series 2)

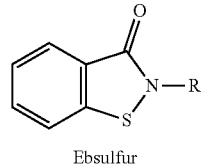
Ebsulfur (Series 3)

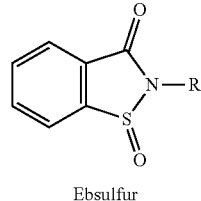
Ebsulfur (Series 4)

TABLE 1

| Cpd # | R | Yeast Strains | | | | | | | | | | Filamentous Fungi | | |
|---|---|---|---|---|---|---|---|---|---|---|---|---|---|---|
| | | A | B | C | D | E | F | G | H | I | J | K | L | M |
| 1 | phenyl | 12.5 | 12.5 | 12.5 | 1.56 | 3.13 | >12.5 | 12.5 | 1.56 | 1.56 | 6.25 | 6.25 | 1.56 | 1.56 |
| 2a | phenyl | 12.5 | >12.5 | 12.5 | 3.13 | 6.25 | >12.5 | >12.5 | 6.25 | 3.13 | 12.5 | 6.25 | 6.25 | 6.25 |
| 2b | 4-F-phenyl | 3.13 | 6.25 | 3.13 | 3.13 | 3.13 | 6.25 | 1.56 | 6.25 | 3.13 | 12.5 | 6.25 | 12.5 | 12.5 |
| 2c | 4-Cl-phenyl | 3.13 | >12.5 | 12.5 | 6.25 | 6.25 | 6.25 | 12.5 | 6.25 | 3.13 | 12.5 | 6.25 | 6.25 | 6.25 |
| 2d | 4-Br-phenyl | 3.13 | 3.13 | 1.56 | 3.13 | 0.78 | 1.56 | 3.13 | 6.25 | 3.13 | 6.25 | 12.5 | 12.5 | 12.5 |

TABLE 1-continued

| Cpd # | R | \multicolumn{10}{c|}{Yeast Strains} | \multicolumn{3}{c|}{Filamentous Fungi} |
|---|---|---|---|---|---|---|---|---|---|---|---|---|---|---|
| | | A | B | C | D | E | F | G | H | I | J | K | L | M |
| 2e | 4-isopropylphenyl | 3.13 | 3.13 | 3.13 | 3.13 | 3.13 | 6.25 | 3.13 | 3.13 | 3.13 | 3.13 | 6.25 | 6.25 | 6.25 |
| 2f | 4-ethynylphenyl | 12.5 | 12.5 | >12.5 | 12.5 | >12.5 | 12.5 | 12.5 | 6.25 | 6.25 | 12.5 | 12.5 | 12.5 | 12.5 |
| 2g | 3-bromopyridyl | >12.5 | 12.5 | 12.5 | 12.5 | >12.5 | 12.5 | 12.5 | 12.5 | 12.5 | 12.5 | 12.5 | 12.5 | 12.5 |
| 2h | 3-isopropylphenyl | 3.13 | 3.13 | 3.13 | 3.13 | 3.13 | 3.13 | 3.13 | 3.13 | 3.13 | 3.13 | 6.25 | 12.5 | 12.5 |
| 2i | 3,5-dibromophenyl | 3.13 | 6.25 | 6.25 | 6.25 | 6.25 | 3.13 | 6.25 | 6.25 | 6.25 | 6.25 | 12.5 | 3.13 | 12.5 |
| 2j | 3,5-dimethylphenyl | 3.13 | 6.25 | 1.56 | 12.5 | 0.78 | 3.13 | 3.13 | 12.5 | 12.5 | 12.5 | 12.5 | 12.5 | 12.5 |
| 2k | 3,5-dimethoxyphenyl | 12.5 | 12.5 | 3.13 | 3.13 | 1.56 | 12.5 | 12.5 | 6.25 | 6.25 | 6.25 | 6.25 | 6.25 | 6.25 |
| 2l | 1-naphthyl | 6.25 | 12.5 | >12.5 | 3.13 | >12.5 | >12.5 | 6.25 | 12.5 | 6.25 | 12.5 | 12.5 | 12.5 | 12.5 |
| 2m | 2-pyridyl | 6.25 | 6.25 | 12.5 | 6.25 | 6.25 | 6.25 | 6.25 | 12.5 | 6.25 | 12.5 | 12.5 | 12.5 | 12.5 |
| 2n | 5-chloro-2-pyridyl | 12.5 | 12.5 | 12.5 | >12.5 | 12.5 | 12.5 | 12.5 | >12.5 | >12.5 | >12.5 | >12.5 | >12.5 | >12.5 |

TABLE 1-continued

| Cpd # | R | Yeast Strains | | | | | | | | | | Filamentous Fungi | | |
|---|---|---|---|---|---|---|---|---|---|---|---|---|---|---|
| | | A | B | C | D | E | F | G | H | I | J | K | L | M |
| 2o | quinolin-2-yl | ND | ND | ND | ND | ND | ND | ND | ND | ND | ND | ND | ND | ND |
| 3a | -(CH2)4-CH3 | 1.56 | 0.39 | 0.78 | 1.56 | 0.39 | 0.78 | 0.78 | 1.56 | 0.78 | 0.78 | ≤0.02 | ≤0.02 | ≤0.02 |
| 3b | -(CH2)5-CH3 | 1.56 | 1.56 | 0.78 | 1.56 | 0.78 | 1.56 | 0.78 | 1.56 | 0.78 | 0.78 | ≤0.02 | ≤≤0.02 | ≤0.02 |
| 3c | -(CH2)7-CH3 | 6.25 | 1.56 | 6.25 | 3.13 | 1.56 | 1.56 | 1.56 | 1.56 | 1.56 | 0.78 | ≤0.02 | ≤0.02 | ≤0.02 |
| 3d | -(CH2)11-CH3 | >12.5 | >12.5 | >12.5 | >12.5 | >12.5 | >12.5 | >12.5 | 12.5 | >12.5 | >12.5 | >12.5 | >12.5 | >12.5 |
| 3e | isobutyl | 0.78 | 1.56 | 0.78 | 0.78 | 0.78 | 0.78 | 1.56 | 1.56 | 0.39 | 0.78 | 0.20 | 0.02 | 0.10 |
| 3f | isopentyl | 1.56 | 0.78 | 1.56 | 0.78 | 0.78 | 0.78 | 1.56 | 1.56 | 0.39 | 1.56 | 0.20 | 0.02 | 0.10 |
| 3g | tert-butyl | 0.78 | 1.56 | 3.13 | 1.56 | 1.56 | 1.56 | 1.56 | 1.56 | 0.78 | 1.56 | 0.10 | 0.10 | 0.10 |
| 3h | benzyl | 0.39 | 1.56 | 1.56 | 1.56 | 1.56 | 1.56 | 0.78 | 1.56 | 0.39 | 0.78 | 0.78 | 0.39 | 0.39 |
| 3i | -(CH2)2-Ph | 1.56 | 1.56 | 1.56 | 1.56 | 1.56 | 1.56 | 1.56 | 1.56 | 1.56 | 1.56 | 0.78 | 0.20 | 0.20 |
| 3j | -(CH2)3-Ph | 6.25 | 3.13 | 6.25 | 3.13 | 6.25 | 6.25 | 6.25 | 1.56 | 1.56 | 6.25 | 0.78 | 0.20 | 0.20 |

TABLE 1-continued

| Cpd # | R | Yeast Strains | | | | | | | | | | Filamentous Fungi | | |
|---|---|---|---|---|---|---|---|---|---|---|---|---|---|---|
| | | A | B | C | D | E | F | G | H | I | J | K | L | M |
| 3k | cyclopentyl | 0.39 | 1.56 | 0.78 | 0.39 | 0.39 | 0.39 | 0.78 | 0.78 | 0.39 | 1.56 | 0.20 | 0.10 | 0.10 |
| 3l | cyclohexyl | 0.78 | 1.56 | 3.13 | 0.78 | 1.56 | 0.78 | 1.56 | 1.56 | 0.78 | 1.56 | 0.20 | 0.20 | 0.20 |
| 3m | cycloheptyl | 1.56 | 1.56 | 3.13 | 1.56 | 3.13 | 1.56 | 3.13 | 3.13 | 0.39 | 3.13 | 0.10 | 0.20 | 0.20 |
| 3n | cyclooctyl | 3.13 | 3.13 | 6.25 | 6.25 | 6.25 | 6.25 | 6.25 | 3.13 | 0.39 | 3.13 | ≤0.02 | 0.05 | ≤0.02 |
| 3o | adamantyl | ND | ND | ND | ND | ND | ND | ND | ND | ND | ND | ND | ND | ND |
| 4e | isopropyl | >12.5 | >12.5 | >12.5 | >12.5 | >12.5 | >12.5 | >12.5 | >12.5 | >12.5 | >12.5 | >12.5 | >12.5 | >12.5 |
| 4f | isobutyl (-(-)₂-) | >12.5 | >12.5 | >12.5 | >12.5 | >12.5 | >12.5 | >12.5 | >12.5 | >12.5 | >12.5 | >12.5 | >12.5 | >12.5 |
| 4n | cyclooctyl | >12.5 | >12.5 | >12.5 | >12.5 | >12.5 | >12.5 | >12.5 | >12.5 | >12.5 | >12.5 | >12.5 | >12.5 | >12.5 |
| AmB | — | 3.9 | 3.9 | 1.95 | 0.98 | 1.95 | 3.9 | 3.9 | 1.95 | 3.9 | 1.95 | 15.6 | 15.6 | 3.9 |
| FLC | — | 62.5[a] | >125[a] | 15.6[a] | >125[a] | >125[a] | 62.5[a] | 62.5[a] | >31.2 | >31.2 | 1.95 | 6.25 | 6.25[a] | 62.5 |
| ITC | — | 0.5[a] | >62.5[a] | 7.8[a] | 31.2[a] | 31.2[a] | 31.2[a] | 31.2[a] | 7.8 | 0.48 | 0.12 | 0.48 | 0.195[a] | 0.975 |
| POS | — | 0.5[a] | >62.5[a] | 7.8a | 31.2[a] | 31.2[a] | 15.6[a] | 15.6[a] | 0.12 | 0.06 | <0.03 | 0.24 | 0.195[a] | 0.48 |
| VOR | — | 7.8 | >31.2 | 0.975 | 1.95 | 1.95 | 0.975 | 7.8 | 0.06 | 0.12 | <0.03 | 0.24 | 0.03 | 0.12 |

Yeast strains: A = *Candida albicans* ATCC 10231, B = *C. albicans* ATCC 64124, C = *C. albicans* ATCC MYA-2876 S), D = *C. albicans* ATCC 90819(R), E = *C. albicans* ATCC MYA-2310(S), F = *C. albicans* ATCC MYA-1237(R), G = *C. albicans* ATCC MYA-1003(R), H = *Candida glabrata* ATCC 2001, I = *Candida krusei* ATCC 6258, J = *Candida parapsilosis* ATCC 22019. NOTE: Here, the (S) and (R) indicate that ATCC reports these strains to be susceptible (S) and resistant (R) to ITC and FLC.
Filamentous fungi: K = *Aspergillus flavus* ATCC MYA-3631, L = *Aspergillus nidulans* ATCC 38163, M = *Aspergillus terreus* ATCC MYA-3633.
Known antifungal agents: AmB = amphotericin B, FLC = fluconazole, ITC = itraconazole, POS = posaconazole, and VOR = voriconazole.
[a]These values were previously reported in Shrestha, S. K. et al. (2015) Amphiphilic tobramycin analogues as antibacterial and antifungal agents. *Antimicrob. Agents Chemother*. 59, 4861-4869.
[b]For yeast strains: MIC-0 values are reported for compounds 1-4n and AmB, whereas MIC-2 values are reported for azoles. For filamentous fungi, MIC-0 values are reported for all copmounds.
ND indicates that MIC values were not determined due to solubility issues with the compound.

The MIC values listed for the controls were either tested herein or acquired from previously published manuscripts on unrelated antifungal agents, which are hereby incorporated by reference in their entirety. Shrestha, S. K. et al. (2015) Amphiphilic tobramycin analogues as antibacterial and antifungal agents. *Antimicrob. Agents Chemother*. 59, 4861-4869. For the controls, AmB, as expected, was the most active against both *Candida* and *Aspergillus* strains with MIC values ranging from 0.98-15.6 µg/mL. Despite its potent antifungal activity, it should be noted that AmB, even with the liposomal formulations, has been well known for its severe and potentially lethal side effects such as nephrotoxicity and hypokalemia. Deray, G. (2002) Amphotericin B nephrotoxicity. *J. Antimicrob. Chemother*. 49 Suppl 1, 37-41; Moen, M. D. et al. (2009) Liposomal amphotericin B: a review of its use as empirical therapy in febrile neutropenia and in the treatment of invasive fungal infections. *Drugs* 69, 361-392. FLC, the most popular and well-tolerated FDA approved antifungal agent, was fairly inactive against the panel of fungal strains presented here, with MIC values mostly from >31.2->125 µg/mL (except against *C. parapsilosis* (strain J), MIC=1.95 µg/mL). ITC, POS, and VOR displayed similar activity against the strains presented here, with MIC values mostly ranging from <0.03-31.2 µg/mL. The azole compounds, however, are potent inhibitors of human cytochrome P450 enzymes, which somewhat limit their applications due to drug-drug interactions with co-administered drugs. Dvorak, Z. (2011) Drug-drug interactions by azole antifungals: Beyond a dogma of CYP3A4 enzyme activity inhibition. *Toxicol. Lett.* 202, 129-132. ITC and VOR are also generally not as well tolerated as FLC. Wang, J. L. et al. (2010) Systematic review and meta-analysis of the tolerability and hepatotoxicity of antifungals in empirical and definitive therapy for invasive fungal infection. *Antimicrob. Agents Chemother.* 54, 2409-2419. To effectively evaluate the activities of the compounds of the invention, poor, good, very good, and excellent activity are respectively defined as ≥12.5 µg/mL, 1.56-6.25 µg/mL, 0.39-0.78 µg/mL, and ≤0.10 µg/mL, respectively.

Ebselen

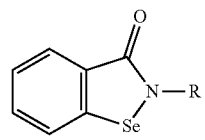

Ebselen

Ebselen (1) was tested first against the panel of *Candida* strains (A-J). Ebselen (1) displayed good activity against strains D, E, H, I, and J (1.56-6.25 µg/mL) and poor activity against strains A, B, C, F, and G (≥12.5 µg/mL). When compared to the controls, these MIC values were generally better than the MIC values of the azoles (except against strains A and H-J), but were worse than those of AmB. Next, ebsulfur (2a) was evaluated. Ebsulfur (2a) displayed a very similar anti-*Candida* profile to that of ebselen (1). In particular, ebsulfur (2a) and ebselen (1) displayed good and poor activity against the same *Candida* strains. With the exception of strain J, 2a was active against strains D, E, H, and I (1.56-6.25 µg/mL) and poorly active against strains A, B, C, F, G, and J (≥12.5 µg/mL). This finding demonstrates that replacing the Se atom with the S atom does not compromise antifungal activity.

Ebsulfur and Ebsulfur 2 Series

Ebsulfur Series 2

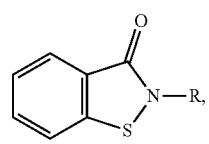

R = substituted or unsubstituted aryl or heteroaryl

Compounds 2b-d were systematically prepared to contain p-substituted halogen atoms that increased in bulkiness with F<Cl<Br. The SAR comparison for these compounds was found to be flat, with all three compounds generally displaying MIC values from 1.56-6.25 µg/mL. Compound 2e displayed good MIC values (3.13-6.25 µg/mL) similar to those of 2b-d. Lastly, p-ethinyl analogue (2f) was found to display mostly poor activity against *Candida* strains (>12.5 µg/mL).

The m-monosubstituted analogues (2g,h) and the 3,5-disubstituted analogues (2i-k) were examined next. While the m-Br substitution of 2g was not beneficial at all (>12.5 µg/mL) against *Candida* strains, the m-iPr (2h), m,m-di-Br (2i), m,m-di-Me (2j), and m,m-di-OMe (2k) analogues were overall better tolerated with good to moderate MIC values (3.13->12.5 µg/mL). By comparing the p-substituted analogues 2d,e and their m-substituted counterparts 2g,h, it was discovered that switching from p-Br (2d) to m-Br (2g) led to loss of activity, whereas switching from p-iPr (2e) and m-iPr (2h) led to compounds which displayed very similar MIC values. Overall, the activity of these compounds appeared to weakly correlate with the number or the positions of the substituents on the phenyl ring.

Analogues with complex aromatic rings, such as the naphthyl (21), pyridyl (2m,n), and quinolinyl (2o), were examined next. Compounds 21,m displayed good to poor activity (6.25->12.5 µg/mL), while compound 2n was poorly active (>12.5 µg/mL) and 2o could not be evaluated due to solubility issues in the RPMI 1640 medium.

Thus, the ebselen 2 series resulted in analogues with mostly good MIC values that are comparable to the parent ebsulfur (2a). In particular, compounds 2d, 2e, 2h, and 2i displayed incrementally improved MIC values when compared to those of ebsulfur (2a).

Ebsulfur 3 Series

Ebsulfur Series 3

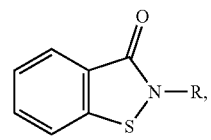

R = substituted or unsubstituted alkyl or cycloalkyl

Inspired by the observation that coupling linear alkyl chains to aminoglycoside antibiotics resulted in a significant improvement of their antifungal activity, ebsulfur analogues with linear alkyl chains of 5-12 carbons ($C_5$, $C_6$, $C_8$, and $C_{12}$, 3a-d) were generated and their antifungal activities were examined. Fosso, M. Y. et al. (2015) Synthesis and bioactivities of kanamycin B-derived cationic amphiphiles. *J. Med. Chem.* 58, 9124-9132; Shrestha, S. K. et al. (2015) Amphiphilic tobramycin analogues as antibacterial and antifungal agents. *Antimicrob. Agents Chemother.* 59,4861-4869; Chang, C. W. and Takemoto, J. Y. (2014) Antifungal amphiphilic aminoglycosides. *Med Chem Comm* 5, 1048-1057; Fosso, M. et al. (2015) Structure-activity relationships for antibacterial to antifungal conversion of kanamycin to amphiphilic analogues. *J. Org. Chem.* 80, 4398-4411; Fosso, M. Y. et al. (2014) New trends in aminoglycosides use. *Med Chem Comm* 5,1075-1091. Because previous work with aminoglycosides where tobramycin and kanamycin analogues with $C_{12}$ and $C_{14}$ alkyl chains displayed the best antifungal activity, it was hypothesized that the ebsulfur analogue with the longest alkyl chain (3d) would be the most active. However, it was surprisingly discovered that ebsulfur analogues with shorter alkyl chains, such as $C_5$ (3a) and $C_6$ (3b), were remarkably effective with very good to good MIC values against all *Candida* strains (0.39-1.56 µg/mL). The $C_8$ analogue (3c) was slightly worse when compared to the $C_5$ (3a) and $C_6$ (3b) analogues (specifically against strains A and C), and the $C_{12}$ analogue (3d) displayed poor MIC values (>12.5 µg/mL).

With respect to anti-Candida, ebsulfur analogue 3a was 20- to 320-fold more potent in MIC values (except against strain J) than FLC. When compared to AmB, ebsulfur analogue 3a was 1.25- to 10-fold more active.

Branched alkyl ebsulfur analogues, such as iso-butyl (3e) and iso-amyl (3f) analogues, were also evaluated. Both 3e and 3f were equally as effective as 3a and 3b (0.39-1.56 µg/mL). In addition, the tent-butyl ebsulfur analogue 3g was also as effective as 3a-f (within 2-fold dilution, 0.78-3.13 µg/mL). Thus, against *Candida* strains, analogues with aliphatic alkyl chains (linear or branched) were found to be very beneficial, which could possibly be attributed to the added rotational flexibility.

In addition, ebsulfur analogues with a phenyl ring connected to the main ebsulfur scaffold via methylene linkers ($C_1$, (3h), $C_2$ (3l), and $C_3$ (3j)) were evaluated. It was found that the $C_1$ and $C_2$-linker analogues (3h,i) had better MIC values compared to 2a (0.39-1.56 µg/mL). However, the $C_3$-linker analogue (3j) was not as potent (1.56-62.5 µg/mL). Thus, it was observed that addition of flexible methylene linkers were well tolerated up to two carbons.

Non-aromatic ring analogues (3k-o) were also evaluated. The cyclopentyl analogue (3k) was found to be just as active (0.39-1.56 µg/mL) as analogues 3a-c. The cyclohexyl analogue (3l) displayed very good to good activity (0.78-3.13 µg/mL), but overall was not as active as analogue 3k. The cycloheptyl (3m) and cyclooctyl (3n) analogues were also not as active as analogues 3k,l. Adamantyl analogue (3o) was not soluble in the RPMI 1640 medium that was used for determination of MIC values. Thus, the SAR showed a modest preference for smaller size ring, as systematically expanding the ring size resulted in a gradual loss in activity. Ebsulfur 4 Series

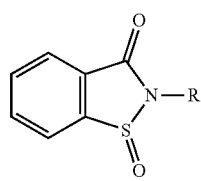

Ebsulfur Series 4

R = substituted or unsubstituted alkyl or cycloalkyl

Lastly, oxidized analogues 4e, 4f, and 4n were tested. It was found that oxidizing the sulfur atom to sulfoxide completely abolished the antifungal activity of the analogues. This finding was in accord with previous reports of these compounds as antibacterials and with other reports in the literature that the biological activity of ebselen (1) and ebsulfur (2a) was highly dependent on the Se—N or S—N bonds. Ngo, H. X. et al. (2016) Development of ebsulfur analogues as potent antibacterials against methicillin-resistant *Staphylococcus aureus*. Bioorg. Med. Chem. doi: 10.1016/j.bmc.2016.03.060; Lu, J. et al. (2013) Ebsulfur is a benzisothiazolone cytocidal inhibitor targeting the trypanothione reductase of *Trypanosoma brucei*. J. Biol. Chem. 288, 27456-27468. Ebselen (1) has been reported to utilize the electrophilic Se—N bond to covalently bind to cysteine residues of multiple enzyme targets.

Invasive aspergillosis is highly correlated with fulminant development and poor prognosis. Compounds with potent anti-*Aspergillus* activity are considered to be of great valuable. Thus, the compounds of the invention were tested against freshly harvested spores of three *Aspergillus* strains: A. flavus (strain K), *A. nidulans* (strain L), and *A. terreus* (strain M). Overall, the compounds of the invention were mostly active against *Aspergillus* strains and the SAR trends observed from the study with *Candida* strains were translatable to *Aspergillus* strains. Aromatic analogues (2a-o) exhibited good to poor activity against strains K-M (1.56-12.5 µg/mL). Linear-chain $C_5$, $C_6$, and $C_8$ analogues (3a-c) displayed excellent activity at ng/mL concentrations (≤0.02-0.20 µg/mL). These results were equivalent or slightly better when comparing them to VOR (0.03-0.24 µg/mL), the gold standard for the treatment of invasive aspergillosis. Other analogues (3e-m) displayed very good activity (0.10-0.78 µg/mL), but they were not as effective as 3a-c. The cyclooctyl analogue (3n) displayed excellent activity against *Aspergillus* strains (≤0.02-0.05 µg/mL). These values were equivalent to analogues 3a-c.

Example 2

Time-Kill Assays

The efficiency of the compounds to kill C. albicans ATCC 64124 (strain B) was monitored using a previously published protocol. The cell suspensions were prepared to achieve an inoculum of approximately $1-4 \times 10^5$ CFU/mL in RPMI 1640 medium at 35° C. 100 µL of cell suspension was added to 900 µL of sterile dd $H_2O$ (control) or to sterile dd $H_2O$ with ebselen, ebsulfur (2a), and 3a at concentrations of 1×, 2×, and 4× their respective MIC values. After fungal cell addition, at 0, 3, 6, 9, 12, and 24 h, the tubes were vortexed and 100 µL aliquots were removed from each solution, spread onto PDA plates, and incubated at 35° C. Colony counts were determined after 24 h of incubation. The experiments were performed in duplicate (FIG. 2).

Figure 2A:
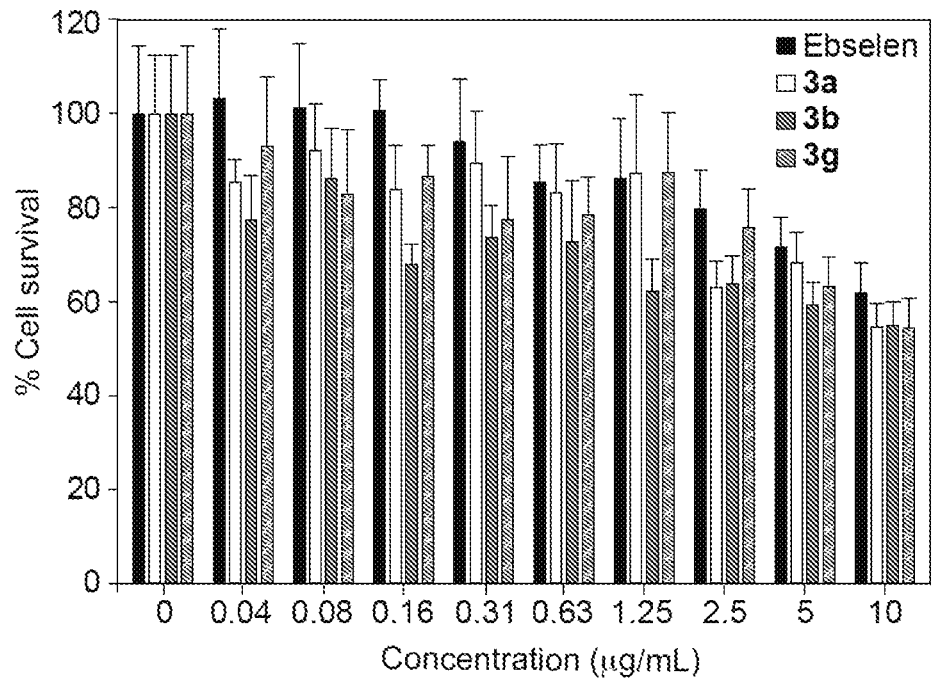
FIG. 2A. Mammalian cell cytotoxicity of ebselen (1) (black bars), and compounds 3a (white bars), 3b (gray bars), and 3g (bars with dashes) was determined against HEK 293 cell line. Triton-X 100® (1%, v/v) was used as the positive control (data not shown).
Figure 2B:
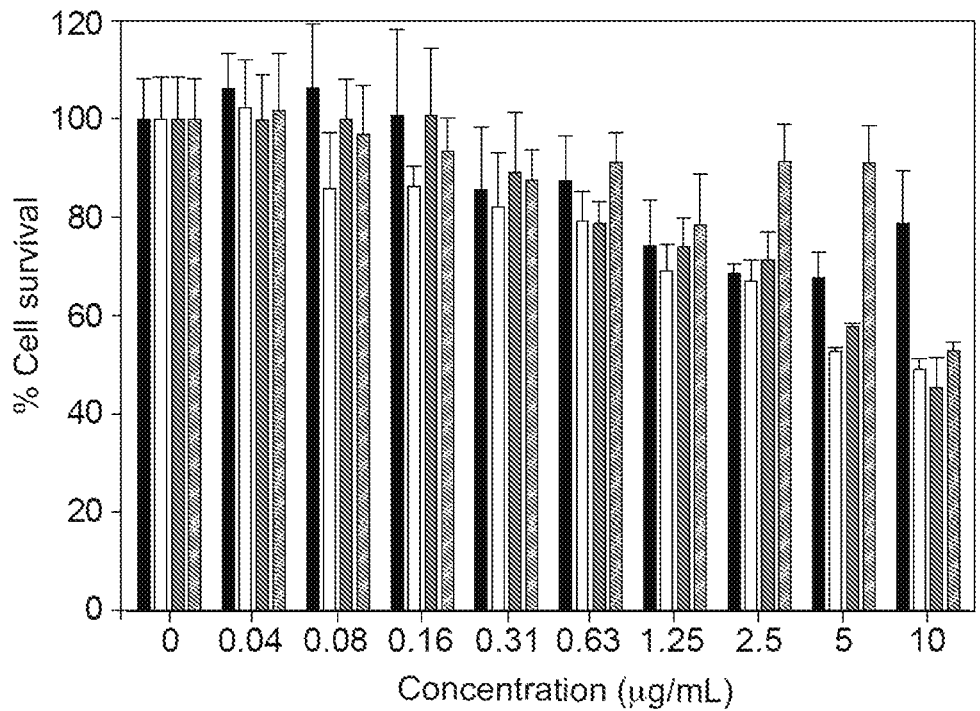
FIG. 2B. Mammalian cell cytotoxicity of ebselen (1) (black bars), and compounds 3a (white bars), 3b (gray bars), and 3g (bars with dashes) was determined against J774 cell line. Triton-X 100® (1%, v/v) was used as the positive control (data not shown).

Time-kill assays with ebsulfur (2a) and analogue 3a (FIG. 2) were performed to determine the rate of fungicidal activity of the compounds of the invention. The results were compared to ebselen (1) and the clinically potent and widely used antifungal agent AmB, which also served as positive control in the time-kill assays. First, all tested compounds (ebselen (1), ebsulfur (2a), 3a, and AmB) were dosed at 1× their respective MIC values (FIG. 2A). Although the MIC value for ebsulfur (2a) against strain B was observed to be greater than 12.5 µg/mL, ebsulfur (2a) was tested at 12.5 µg/mL due to concerns that higher concentration may lead to precipitation of the compounds. Ebselen (1) (at 12.5 µg/mL) displayed potent fungicidal activity leading to complete fungal cell death at the 6-h mark, which was even quicker than AmB (at 3.9 µg/mL). Ebsulfur (2a) (at 12.5 µg/mL) and ebsulfur analogue 3a (at 0.39 µg/mL) displayed fungistatic effects. However, at their 1× MIC, ebsulfur (2a) and 3a were not able to completely inhibit fungal re-growth even after 24 h incubation. Hence, the doses of these compounds were doubled in additional time-kill analysis experiments.

At 2× MIC (FIG. 2B), Ebselen (1) (at 25 µg/mL) and AmB (at 7.8 µg/mL) were completely fungicidal from 3 and 6 h, respectively. At the higher concentration, ebsulfur (2a) (25 µg/mL) became fungicidal. Compound 3a (at 0.78 µg/mL) remained fungistatic with a 4-log reduction of fungal cells at approximately the 24-h mark. When, the concentration of compound 3a was increased to 4× its MIC value (at 1.56 µg/mL), compound 3a remained fungistatic (FIG. 2C). These findings suggested that, to be effective antifungal agents, ebsulfur (2a) and compound 3a would have to be dosed at least 2× their respective MIC values. However, ebselen (1) could still be effective at 1× MIC.

Example 3

Hemolytic Assays

Figure 3:
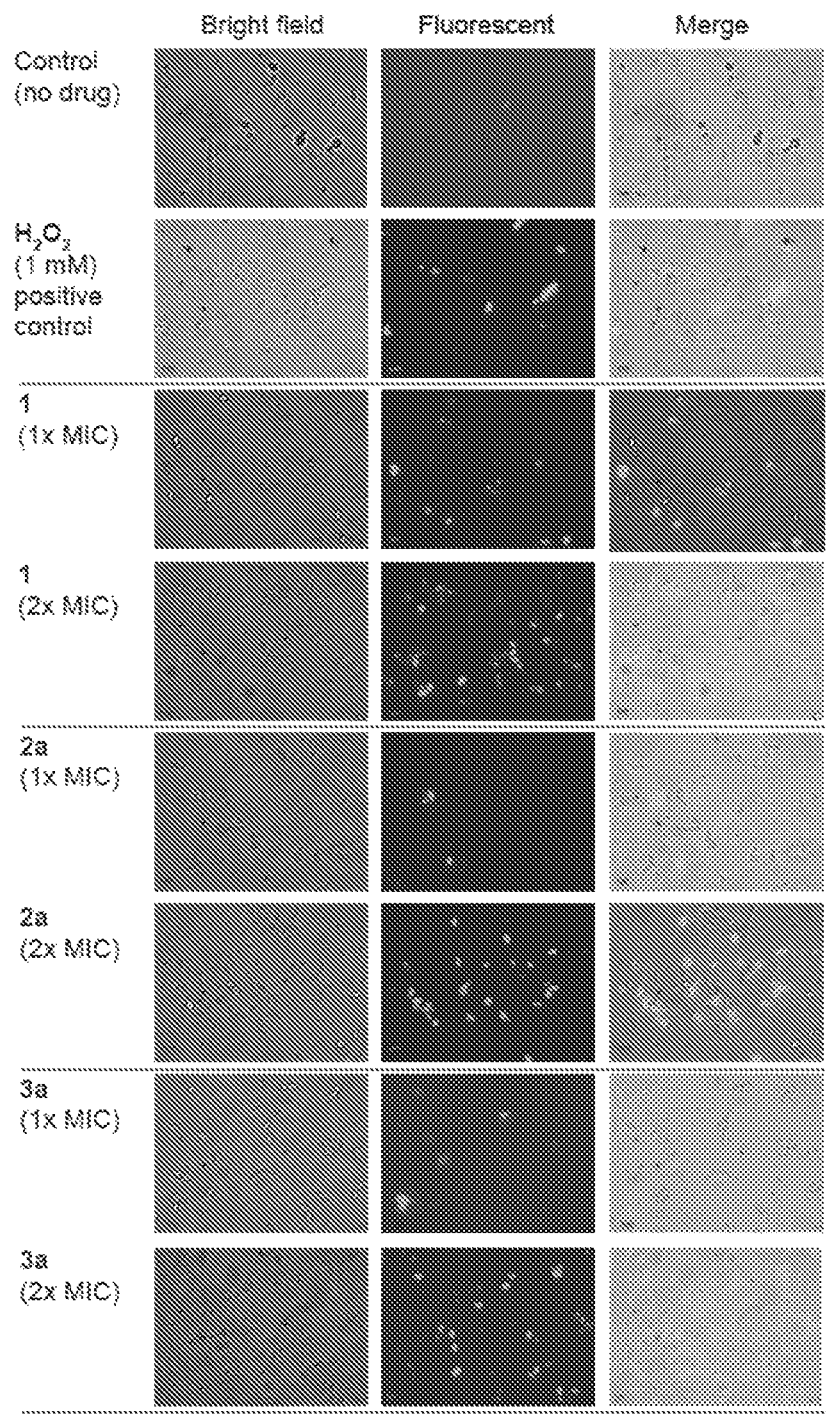
FIG. 3. ROS induction assay of ebselen (1), ebsulfur (2a), and compound 3a was performed against *C. albicans* ATCC 10231 (strain A). Candida cells were treated with no drug (negative control), 1 mM of $H_2O_2$ (positive control), or ebselen, 2a, and 3a at their 1× and 2× respective MIC values for 1 h at 37° C. DCFH-DA (40 µg/mL) was added to detect ROS and the samples were analyzed using a Zeiss Axovert 200M fluorescence microscope.

Hemolytic activity was determined as previously described with minor modifications (FIG. 3). Shrestha, S. K. et al. (2015) A combination approach to treating fungal infections, *Sci. Rep.* 5, 17070. Murine red blood cells (mRBCs) (1 mL) were suspended in 9 mL of phosphate buffer saline (PBS; 10 mM, pH 7.2) and then centrifuged (1,200 rpm) for 10 min at room temperature. mRBCs were washed with PBS 4 times and then resuspended in fresh PBS (5 mL) to achieve the final concentration of ($1\times10^7$ mRBCs/mL). Compounds were serially diluted in Eppendorf tubes containing $H_2O$ (100 µL). The mRBC suspension was then added to achieve final concentrations ranging from 31.2-0.24 µg/mL and $5\times10^6$ mRBCs/mL of tested compounds and mRBCs, respectively. The tubes were then incubated for 1 h at 37° C. Tubes containing dd $H_2O$ (200 µL) and triton X-100® (1% v/v, 2 µt) served as negative (blank) and positive (100%) control, respectively. The percent hemolysis was calculated using the following equation: % hemolysis= [(absorbance of sample)−(absorbance of blank)]×100/(absorbance of positive control). Fifty percent hemolysis ($HC_{50}$) values were defined as the concentrations of compounds required to lyse 50% of the mRBCs.

Previous studies of aminoglycoside analogues reported that aminoglycoside analogues with linear alkyl chains could be toxic to red blood cells (RBCs) because, due to their ultra-thin cell membranes, RBCs are prone to hemolysis. Therefore, analogues with linear alkyl chains, such as the $C_5$ analogue 3a and the $C_8$ analogue 3c, were tested against murine red blood cells (mRBCs) and compared to ebselen (1) (FIG. 3). Most of the tested compounds (ebselen (1), ebsulfur (2a), and compound 3c) did not show significant hemolytic activity until 15.6 µg/mL. Although compound 3a initially appeared to be hemolytic at approximately 3.9 µg/mL, this compound exhibited remarkable potency against fungal cells. The MIC values of compound 3a were at least 5- to 195-fold lower than the hemolytic concentrations for *Candida* and *Aspergillus* strains, respectively. Thus, some cytocidal selectivity towards fungal cells was observed.

Example 4

Mammalian Cytotoxicity Assay

Compounds 3a, 3b, and 3g (in terms of their overall antifungal activity against both *Candida* and *Aspergillus* strains) were evaluated against two different mammalian cell lines, which have normal cell membranes and are not susceptible to membrane-lytic compounds.

Mammalian cytotoxicity assays were performed as previously described with minor modifications (FIG. 4). The HEK-293 and J774A.1 cell lines were grown in various Dulbecco's Modified Eagle's Medium (DMEM) with 10% fetal bovine serum (FBS) and 1% Pen/Strep at 37° C. with 5% $CO_2$. The confluent cells were either trypsinized with 0.05%-trypsin-0.53 mM EDTA (HEK-293 cell line) or mechanically removed by cell scrapers (J774A.1 cell line). The cells were transferred into 96-well microtiter plates at a density of $1\times10^4$ cells/mL (HEK-293 cell line) or $2\times10^4$ cells/mL (J774A.1 cell line) and were grown for 16 h overnight. The following day, the media were replaced by fresh media (100 µL) containing no compound (negative control), triton-X 100® (positive control) (1%, v/v), and serially diluted ebselen (1), 3a, 3b, and 3g at final concentrations of 10-0.02 µg/mL. Every well contained 0.1% DMSO, which is not toxic against these mammalian cell lines. The cells were incubated with tested compounds for another 24 h at 37° C. with 5% $CO_2$. Cell survival was assessed by resazurin assay. Each well was treated with resazurin (10 µL of a 25 mg/L solution) for 6 h. Live cells produced the highly fluorescent pink dye resorufin, which was detected at $\lambda_{560}$ absorption and $\lambda_{590}$ emission by a SpectraMax M5 plate reader. Dead cells remain purple/blue. The percentage of survival rate was calculated by using the following formula: [(test value)/(control value)×100]. The control value is obtained from the wells, which have cells and resazurin, but no tested compounds.

ROS production assay was performed as previously described with minor modifications. The 2',7'-dichlorodihydrofluorescein diacetate (DCFH-DA) probe was used to measure the production of ROS in fungal cells after treatment of cells with ebselen, ebsulfur (2a), and 3a. Once entering the cells, the DCFH-DA probe is first hydrolyzed to the non-fluorescent 2',7'-dichlorodihydrofluorescein (DCFH) by cellular esterases. After that, DCFH is oxidized to the highly fluorescent 2',7'-dichlorofluorescein (DCF) by intracellular ROS. A colony of *C. albicans* ATCC 10231 (strain A) was used to inoculate 5 mL of PDB in a Falcon tube and grown overnight at 35° C. at 200 rpm. In the morning, the culture was diluted by addition of fungal cells (200 µL) to RPMI 1640 medium (800 After that, newly diluted cell suspension (100 µL) was added to the RPMI 1640 medium (900 µL) containing no drug (negative control) or ebselen, 2a, and 3a, at their 1× and 2× MIC values and incubated for 1 h at 37° C. Glass slides (with 10-15 of each mixture) were prepared and observed in bright field and fluorescence modes (FITC filter set, $\lambda_{ex}$=488 nm and $\lambda_{em}$=512 nm excitation) using a Zeiss Axovert 200M fluorescence microscope (FIG. 5).

Compounds 3a, 3b, and 3g were evaluated for their cytotoxicity against HEK293 and J774 cell lines using a resazurin assay. The percentage of surviving cells treated with the analogues versus the percentage of surviving cells treated was compared with ebselen (1) (FIG. 4). Against the HEK293 cell line (FIG. 4A), the analogues (3a, 3b, and 3g) were observed to be slightly more toxic but overall, quite comparable to ebselen (1) at all concentrations tested. Overall, all the tested compounds (ebselen (1), 3a, 3b, and 3g) induced approximately 50 to 40% cell death at 10 µg/mL (FIG. 4A). The similarity of cytotoxicity data of ebselen (1) found in the present study to other reported in vitro mammalian cytotoxicity studies of ebselen (1) was verified. Given the good tolerability of ebselen (1) during clinical trials, it was intriguing to us that compounds 3a and 3b displayed similar in vitro cytotoxicity. The HEK293 cell line was chosen to determine the potential for kidney injury. The kidney is a highly perfused organ and comes in contact with many compounds due to renal excretion. Thus, many compounds such as AmB are highly nephrotoxic and cause great burden to patients with compromised renal function.

Next, the compounds were evaluated against J774 (FIG. 4B), a murine macrophage cell line. This cell line was selected to test that the compounds would not interfere with the survival of host macrophages, because macrophages are the first-line of defense against fungal infection. Against the J774 cell line, a trend similar to the HEK293 cell line was observed. It was found that analogues (3a and 3b) were slightly more toxic but still comparable to ebselen (1) with approximately 50% cell death at 10 µg/mL. Compounds 3g did not show any toxicity up to 5 µg/mL.

Example 5

ROS Production

Although there are concerns in the literature regarding the highly reactive isothiazolinone moiety of the ebsulfur (2a) scaffold, the scaffold merits further consideration and optimization as a possible antifungal candidate based on two particular reasons. First, since many potent antifungal compounds are only available intravenously (e.g., polyenes and echinocandins), there is currently a dire clinical need for orally active antifungals to assist the azoles as an alternative option for step-down therapy. As of 2016, the IDSA clinical practice guideline recommends the use of step-down therapies for many invasive fungal diseases. These azoles, however, often complicate drug dosing and require many dose adjustments for numerous immunocompromised patients due to interactions with the metabolism of anticancer and antiretroviral drugs. Additionally, some pathogenic fungal strains are increasingly resistant to FLC, the most popular azole, especially in patients who experience previous FLC administration. Ebselen was successfully administered orally during both phase 1 and 3 clinical trials. Due to its structural similarity to ebselen (1), the ebsulfur (2a) scaffold would most likely be orally active and potentially be a highly valuable addition to the current step-down therapy. Second, while there are concerns about the high reactivity of the isothiazolinone moiety towards cysteine residues, ebselen (1) with the isoselenazolinone moiety has been shown to be well-tolerated during clinical trials. Additionally, there are also examples of other clinically successful small-molecule inhibitors with highly reactive chemical moieties within the FDA-approved chemical space. Some of these compounds are penicillin, fosfomycin, or bendamustine. As in many cases, it is often the dose that determines the poison.

Compounds 3a and 3b displayed MIC values against clinically relevant *Candida* strains at 780 ng/mL and *Aspergillus* strains at ≤20 ng/mL. This difference in fungal and mammalian toxic concentrations could be due to the stronger binding affinity that compounds 3a and 3b have for fungal target(s) compared to the binding affinity that they have for mammalian targets. Thus, ROS induction of ebsulfur analogues was studied to understand the mechanism of action of these compounds.

Recently, it was shown that ebselen (1) and the ebsulfur analogues with antibacterial activity were highly correlated with ROS production in MRSA bacterial cells. It was also reported that ebselen (1) induced ROS-mediated cytotoxicity in *Saccharomyces cerevisiae*. Thus, whether the compounds of the invention would also induce ROS against *C. albicans* was studied. Ebselen (1), ebsulfur (2a), and compound 3a were tested against *C. albicans* ATCC 10231 cells (strain A) at 1× and 2× their respective MIC values. 2',7'-dichlorodihydrofluorescin diacetate (DCFH-DA) was then used to detect and visualize ROS production (FIG. 5). As a positive control, cells were treated with $H_2O_2$, which is an inducer of hydroxyl radical formation. After 1-h treatment, all the compounds tested and the positive control were found to be highly fluorescent, indicating ROS induction. Samples that were treated with different doses of compounds (1× and 2× their respective MIC values) were also compared, and it was observed that the amount ROS induction could be concentration dependent. It is unclear, however, whether this ROS induction in *C. albicans* spp. is due to inhibition of a specific fungal enzyme responsible for ROS regulation or it is a downstream secondary effect as the ebselen (1) and ebsulfur (2a) scaffolds inhibit enzymes that are unrelated to ROS generation.

Example 6

Pharmacokinetic and Pharmacodynamic Studies

Maximum Tolerated Dose Studies. Maximum tolerated dose studies are conducted. Three "low", "medium", and "high" doses of compounds of formula (I) are selected based on previous ebselen animal studies. The low dose is 15 mg/kg, the medium dose is 30 mg/kg, and the high dose is 45 mg/kg (Ozyigit et al. 2015). The ebsulfur analogues are dissolved in 1 mL of 10% Tween 80 (Sigma-Aldrich, St. Louis, Mo., USA). Healthy outbred CD-1 (Charles River, the Netherlands) female mice from 4 to 5 weeks old, weighing between 20 to 25 g, are randomized to 4 treatment groups of sham, low, medium, and high dose treatment. Each group contains three mice. On the day of treatment, mice in each treatment group receive the appropriate intravenous (IV) doses of vehicle, low, medium, and high dose. Body changes and other signs of toxicity of the treated mice are monitored over a period of 2 weeks. Common signs of toxicity include weight loss, shakiness, distress, etc. Mice observed losing more than 15% body weight are euthanized. The maximum tolerated dose is determined as the dose that causes unacceptable side effects or signs of toxicity.

Bioanalytical Method Development. Next, bioanalytical methods are developed and the lower limit of detection dose is determined for the selected compounds of formula (I) using reversed-phase high-performance liquid chromatography (HPLC). Masses of the compounds are confirmed by Q-TOF Tandem Mass Spectrometer.

Pharmacokinetic Studies. Doses chosen for pharmacokinetics studies are determined by the lower limit of detection dose and the maximum tolerated doses. Healthy outbred CD-1 female mice from 4 to 5 weeks old, weighing between 20 to 25 g are used. For each dose, mice are randomly divided into 2 h, 4 h, 8 h, 12 h, and 24 h treatment groups. There are three mice for each time point. At each time point, the blood sample is collected to determine plasma drug concentration by saphenous vein bleed (50 µL of whole blood). Geometric mean concentrations of total drug in plasma are calculated for each time point. Pharmacokinetic parameters are derived using noncompartmental analysis.

Distribution Studies. Next, the extent of distribution of compounds of formula (I) into certain tissues such as liver, lung, heart, or kidney is determined. Experimental conditions used in the pharmacokinetic studies are repeated. Mouse organs are collected, tissue extractions are performed, and the previously determined bioanalytical method to quantify drug concentrations is used to compare compound concentrations in organs to compound concentrations in the plasma. Of particular interest is the study of compound concentration in the lungs with respect to pulmonary Aspergillosis infections.

Pharmacodynamic Studies. Doses of compounds of formula (I) are selected to perform pharmacodynamics (PD) experiment to understand whether the compounds are effective in clearing *Candida* spp. and *Aspergillus* spp. in vivo. Clinical *C. albicans, C. glabrata,* and *A. fumigatus* isolates are obtained from patients at University of Kentucky Medical Center. An infection model for pharmacodynamic studies reported by Seyedmousavi et al. 2014 is used. CD-1 female mice, 4 to 5 weeks old, weighing 20 to 25 g are randomized into three treatment groups: placebo, ebsulfur analogue, and itraconazole with three mice per group. In order to infect the mice, the mice are first treated with cyclophosphamide (150 mg/kg on days −4 and +4, and 100 mg/kg on day −1). On day 0 and 2 h after drug treatments, mice are infected with *C. albicans, C. glabrata, A. fumigatus* isolates. For the blood infection models of *C. albicans* and *C. glabrata,* mice are given inoculum iv. For the special pulmonary *Aspergillosis* mouse model, mice are infected via instillation of the inoculum through the animals' nares using a well-established procedure in the literature. The inoculum size is determined to be corresponding to the $LD_{90}$ (lethal dose, 90%) of the mice. The infected mice are treated with the appropriate treatments based on their assigned groups. Survival in days post-infection are recorded for each mouse in each group. Clinical toxicity effects are monitored. Mice demonstrating acute signs of disease are humanely euthanized. On day 15 post-infection, all surviving mice are euthanized.

Topical Treatment Studies. Eight-week old female BALB/c mice are used for topical treatment studies (Harlan Laboratories, Indianapolis, Ind.) (Thangamani et al. 2015). Mice are injected intradermally with an inoculum of a dermatophyte fungal strain. After 48 h, the site of infection develops into an open wound. The mice are randomized into 5 groups of 3 mice in each. One group receives petroleum jelly alone. Three groups receive 0.5%, 1%, and 2% ebsulfur analogue in petroleum jelly. The fifth group receives the FDA-approved drug Lamisil or terbinafine product. All groups are treated twice a day for 5 days. After the last treatment, recovery of each group is monitored.

Example 7

Agricultural Studies

Honeybee toxicity. The published methods by the U.S. Environmental Protection Agency (EPA) Office of Prevention, Pesticides, and Toxic Substances (OPPTS) are followed with minor modifications (EPA, US 1996). As recommended by the OPPTS, *Apis mellifera* species is used. Worker honeybees are seized at the entrance of a single healthy hive the day of use. The bees are brought to the laboratory and kept in a small cage at room temperature. Honey bees are first anesthetized with $CO_2$ before use and transferred to three individual cups having total of 10 bees in each cup. To evaluate the toxicity effect of ebsulfur compounds against honeybees, acute oral and acute contact tests are performed. To perform acute oral toxicity, honeybees are fed with 200 µL of different concentrations of ebsulfur compounds. Likewise, to perform acute contact test, honeybees are anesthetized again with $CO_2$ and different concentrations of ebsulfur compounds are applied in 1 µL drops to the ventral side of the thorax of each bee. After treatments, the bees are fed with 3 mL of sucrose solution (50% volume of sucrose and 50% volume of water). The cups are stored at 28° C. incubator for 48 h and are checked every 4 h. The ratio of living to dead bees is recorded. The treatments with each concentration are replicated at least thrice.

Leaf Infection Assay. The published protocol by Chang et al. (2010) is followed to perform leaf and wheat head spikelets infection assays. Rapidly maturing wheat cultivar Apogee (Bugbee et al. 1997) is used for this experiment. The phytotoxic effect of compounds of formula (I) are evaluated by applying the compounds on the leaf of wheat plant. To achieve this, various concentrations of compounds of formula (I) at 2×MIC, 6×MIC and 20×MIC are prepared in 0.25% (w/v) agar and 0.2% (v/v) Tween® 20 solution and on leaf. Next, *F. graminearum* spores are mixed at the final concentration of 1×10⁴ macroconidia/mL along with the compounds of formula (I) at each concentration. Finally, the phytotoxic effect of the compounds of formula (I) on wheat plant and the development of infection by *F. graminearum* is assessed. Development of leaf lesion and chlorosis is monitored to analyze either the phytotoxic effect or the establishment of infection by *F. graminearum* in wheat.

Wheat Head Spikelets Infection Assay. The published protocol by Chang et al. (2010) is followed to perform wheat head spikelets infection assay. Rapidly maturing wheat cultivar Apogee (Bugbee et al. 1997) is used for this experiment. Wheat cultivar Apogee is grown for 5-6 weeks in a greenhouse to the flowering stage. The florets (one per spikelet) are first treated with various concentrations of compounds of formula (I) at 2×MIC, 6×MIC and 20×MIC and then are inoculated by F. graminearum macroconidia. The development of disease symptoms such as chlorosis, spikelet curling and dehydration is recorded after 4 days.

The foregoing description and examples have been set forth merely to illustrate the invention and are not meant to be limiting. Since modifications of the described embodiments incorporating the spirit and the substance of the invention may occur to persons skilled in the art, the invention should be construed broadly to include all variations within the scope of the claims and equivalents thereof.

The invention claimed is:

1. A method of treating an infection caused by a fungal species, comprising administering to a subject in need thereof a therapeutically effective amount of a compound of formula (I):

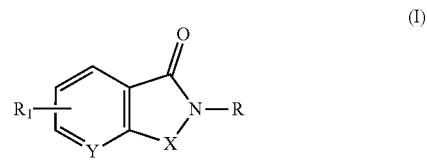

wherein

X is Se, S, or S=O;

Y is C, N, or O;

R is substituted or unsubstituted aryl, substituted or unsubstituted heteroaryl, substituted or unsubstituted alkyl, substituted or unsubstituted cycloalkyl, or $OR_a$;

$R_1$ is —H, —OH, —$NH_2$, $OR_b$, $CF_3$, $NO_2$, or CN;

$R_a$ is linear or branched $C_{1-16}$ alkyl groups or linear pegylated $C_{4-16}$ alkyl groups; and $R_b$ is linear or branched $C_{1-16}$ alkyl groups;

or a salt thereof.

2. A method as in claim 1, wherein X is Se; R is phenyl; or a salt thereof.

3. A method as in claim 1, wherein X is S; R is substituted or unsubstituted aryl, substituted or unsubstituted heteroaryl, substituted or unsubstituted alkyl, or substituted or unsubstituted cycloalkyl; or a salt thereof.

4. A method as in claim 1, wherein X is S=O; R is substituted or unsubstituted aryl, substituted or unsubstituted heteroaryl, substituted or unsubstituted alkyl, or substituted or unsubstituted cycloalkyl; or a salt thereof.

5. A method as in claim 1, wherein the fungal species is selected from the group consisting of *Candida, Aspergillus, Trichophyton, Fusarium, Microsporum, Blumeria, Podosphaera, Sphaerotheca, Phakopsora, Puccinia, Uromyces, Peronospora, Phytophthora, Plasmopara, Pythium, Alternaria, Cercospora, Cladiosporium, Colletotrichum, Cycloconium, Cochhobolus, Gloeosporium, Glomerella, Guignardia, Leptosphaeria, Magnaporthe, Botrytis, Penicillium, Sclerotinia, Verticillium, Rhizoctonia, Sclerotium, Nectria, Monilinia*, and *Helminthosporium* species.

6. A method as in claim 5, wherein the *Candida* species is selected from the group consisting of *Candida albicans, Candida glabrata, Candida krusei*, or *Candida parapsilosis*.

7. A method as in claim 5, wherein the *Aspergillus* species is selected from the group consisting of *Aspergillus flavus, Aspergillus nidulans*, and *Aspergillus terreus*.

8. A method as in claim 1, wherein the subject is a mammal.

9. A method as in claim 1, wherein the subject is an agricultural crop.

* * * * *